(12) United States Patent
Robbins et al.

(10) Patent No.: US 6,936,468 B2
(45) Date of Patent: Aug. 30, 2005

(54) USE OF TOLEROGENIC DENDRITIC CELLS FOR ENHANCING TOLEROGENICITY IN A HOST AND METHODS FOR MAKING THE SAME

(75) Inventors: Paul David Robbins, Mt. Lebanon, PA (US); Lina Lu, Allison Park, PA (US); Nick Giannoukakis, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 135 days.

(21) Appl. No.: 09/844,915

(22) Filed: Apr. 27, 2001

(65) Prior Publication Data

US 2002/0048564 A1 Apr. 25, 2002

Related U.S. Application Data

(60) Provisional application No. 60/200,479, filed on Apr. 28, 2000.

(51) Int. Cl.[7] .......................... C07H 21/04; C12Q 1/68; C12N 5/08
(52) U.S. Cl. .......................... 435/455; 6/325; 536/23.1; 536/24.31
(58) Field of Search .......................... 514/44; 424/93.7, 424/93.21, 550, 529, 553; 536/24.5, 23.1; 435/240.1; 604/93

(56) References Cited

U.S. PATENT DOCUMENTS 5,871,728 A * 2/1999 Thomson et al.
2002/0164311 A1 * 11/2002 Storm et al.

FOREIGN PATENT DOCUMENTS

WO 9535032 12/1995

OTHER PUBLICATIONS

Lu et al. Genetic enginnering of dendritic cells to express immunosuppressive molecules (viral IL-10, TGF-beta and CTLA4lg). Journal of Leukocyte Biology, 1999 vol. 66:293-296.*
Bielinska et al. Regulation of Gene Expression with Double-Stranded Phosphorothioate Oligonucleotides. Science, 1990 vol. 250:997-1000.*
Lu et al. Adenoviral delivery of CTLA4lg into myeloid dendritic cells promotes their in vitro tolerogenicity and survival in allogeneic reciepients. Gene Therapy, 1999 vol. 6:554-563.*
Xu et al. Prolongation of liver allograft survival by dendritic cells modified with NF-kB decoy oligodeoxynucleotides. World Journal of Gastroenterology, 2004 vol. 10:2361-2368.*
Ma et al. Prevention of Diabetes in NOD Mice by Administration of Dendritic Cells Deficient in Nuclear Transcription Factor-kB Activity. Diabetes, 2003 vol. 52:1976-1985.*

(Continued)

*Primary Examiner*—John L. LoGuyader
*Assistant Examiner*—Terra C. Gibbs
(74) *Attorney, Agent, or Firm*—Baker Botts LLP

(57) ABSTRACT

The present invention relates to tolerogenic mammalian dendritic cells (DCs) and methods for the production of the tolerogenic DCs. In addition, the present invention provides a method for enhancing tolerogenicity in a host comprising administering the tolerogenic mammalian DCs of the present invention to the host. The tolerogenic DCs of the present invention comprise an oligodeoxyribonucleotide (ODN) which has one or more NF-κB binding sites. The tolerogenic DCs of the present invention may further comprise a viral vector, and preferably an adenoviral vector, which does not affect the tolerogenicity of the tolerogenic DCs when present therein. Enhanced tolerogenicity in a host is useful for prolonging foreign graft survival and for treating inflammatory related diseases, such as autoimmune diseases.

7 Claims, 25 Drawing Sheets

OTHER PUBLICATIONS

Bohham et al. Marked Prolongation of Cardiac Allograft Survival by Dendritic Cells Genetically Engineered with NF–kB Oligodeoxyribonucleotide Decoys and Adenoviral Vectors Encoding CTLA4–lg. Journal of Immunology, 2002 vol. 169:3382–3391.*

Giannoukakis et al. Prolongation of Cardiac Allograft Survival using Dendritic Cells treated with NF–kB Decoy Oligodeoxyribonucleotides. Molecular Therapy, 2000 vol. 1:430–437.*

Morelli et al. Recombinant adenovirus induces maturation of dendritic cells via an NF–KB dependent pathway. Journal of Virology, 2000 vol. 74:9617–9628.*

Rea et al. Adenoviruses activate human dendritic cells without polarization toward a T–helper type 1–inducing subset. Journal Virology, 1999 vol. 73:10245–10253.*

Zhong et al. Recombinant adenovirus is an efficient and non–pertubing genetic vecotr for human dendritic cell. European Journal of Immunology, 1999 vol. 29:964–972.*

Tillman et al. Maturation of dendritic cells accompanies high–efficiency gene transfer by a CD40–targeted adenoviral vecotr. Journal of Immunology, 1999 vol. 162:6378–6383.*

Flores–Romo In vivo matuation and migration of dendritic cells. Immunology, 2001 vol. 102:255–262.*

Liang et al. "Phenotype and allostimulatory function of dendritic cells treated with antisence oligonucleotides targeting CD80 or CD86 mRNA," Transplantation Proceedings, vol. 33, No. 1–2 p. 235.

Takayama et al. "Transduction of dendritic cell progenitors with a retroviral vector encoding viral interleukin–10 and enhanced green fluorescent protein allows purification of potientially tolerogenic antigen–presenting cells". Transplantation vol. 68, No. 12, pp. 1903–1909, Dec. 1999.

Thomson et al. "Are dendritic cells the key to liver transplant tolerance?" Immunology Today, vol. 20, No. 1, pp. 27–32, Jan. 1999.

Ma et al., "Dual modifications, NF–κB deficiency and overexpression of IL–10, enance DC tolerogenic activity," presented at American Transplant Congress 2003, May 30–Jun. 4, Washington, DC.

Bonham et al., "Marked prolongation of cardiac allograft survival by dendritic cells genetically engineered with NFκB oligonucleotide decoys and adenoviral vectors encoding CTLA4–Ig[1]," Journal of Immunology, 2002, 169:3382–3391.

Hirano et al., "Graft hyporeactivity induced by immature donor–derived dendritic cells," Transplant Proc. 32:260–264 (2000).

Gao et al., "CD40–deficient dendritic cells producing interleukin–10, but not interleukin–12, induc T–cell hyporesponsiveness in vitro and prevent acute allograft rejection," Immunology 98 :159–170 (1999).

Lee et al., " Cyclosporine A inhibits the expression of costimulatory molecules on in vitro–generated dendritic cells: association with reduced nuclear translocation of nuclear factor kappa B,"Transplantation 68:1255–1263 (1999).

Lu et al., "Genetic engineering of dendritic cells to express immunosuppressive molecules (viral IL–10, TGF–beta, and CTLA4Ig)," J. Leukoc. Biol. 66:293–296 (1999).

Lu et al., " Adenoviral delivery of CTLA4Ig into myeloid dendritic cells promotes their in vitro tolerogenicity and survival in allogeneic recipients,"Gene Ther. 6:554–563 (1999).

Ranieri et al., " Dendritic cells transduced with an adenovirus vector encoding Epstein–Barr virus latent membrane protein 2B: a new modality for vaccination,"J. Virol. 73:10416–10425 (1999).

Rea et al., "Adenoviruses activate human dendritic cells without polarization toward a T–helper type 1–inducing subset,"J. Virol. 73:10245–10253 (1999).

Thomson and Lu, "Dendritic cells as regulators of immune reactivity: implications for transplantation," Transplantation 68:1–8 (1999).

Tuting et al.,"Dendriitc cell–based genetic immunization in mice with a recombinant adenovirus encoding murine TRP2 induces effective anti–melanoma immunity," J. Gene Med. 1:400–406 (1999).

Banchereau and Steinman, "Dendritic cells and the control of immunity," Nature 392:245–252 (1998).

Khanna et al., " Donor bone marrow potentiates the effect of tacrolimus on nonvascularized heart allograft survival: association with microchimerism and growth of donor dendritic cell progenitors from recipient bone marrow," Transplantation 65:479–485 (1998).

Lee et al.,"Phenotype, function, and in vivo migration and survival of allogeneic dendritic cell progenitors genetically engineered to express TGF–beta,"Transplantation 66:1810–1817 (1998).

Lu et al. Journal of Leukocyte Biology Supplement 2 Abstract#B52 (1998).

Rescigno et al.,"Dendritic cell survival and maturation are regulated by different signaling pathways," J. Exp. Med. 188:2175–2180 (1998).

Lu et al., "Blockade of the CD40–CD40 ligand pathway potentiates the capacity of donor–derived dendritic cell progenitors to induce long–term cardiac allograft survival," Transplantation 64:1808–1815 (1997).

Fu et al., "Costimulatory molecule–deficient dendritic cell progenitors induce T cell hyporesponsiveness in vitro and prolong the survival of vascularized cardiac allografts," Transplant Proc. 29:1310 (1997).

Fu et al., "Costimulatory molecule–deficient dendritic cell progenitors (MHC class II+, CD80dim, CD86–) prolong cardiac allograft survival in nonimmunosuppressed recipients," Transplantation 62:659–665 (1996).

Lu et al., "Induction of nitric oxide synthase in mouse dendritic cells by IFN–gamma, endotoxin, and interaction with allogeneic T cells: nitric oxide production is associated with dendritic cell apoptosis," J. Immunol. 157:3577–3586 (1996).

Lu et al.," Bone marrow–derived dendritic cell progenitors (NLDC 145+, MHC class II+, B7–1dim, B7–2–) induce alloantigen–specific hyporesponsiveness in murine T lymphocytes," Transplantation 60:1539–1545 (1995).

Rastellini et al.," Granulocyte/macrophage colony–stimulating factor–stimulated hepatic dendritic cell progenitors prolong pancreatic islet allograft survival,"Transplantation 60:1366–1370 (1995).

Andrews and Faller, " A rapid micropreparation technique for extraction of DNA–binding proteins from limiting numbers of mammalian cells,"Nucleic Acids Res. 19:2499 (1991).

Jolly, D., "Viral vector systems for gene therapy,"*Cancer Gene Therapy*, 1:51–64. (1994).

Starzl et al.,"The biological basis of and strategies for clinical xenotransplantation," *Immunological Reviews 141*:213 (1994).

Woo et al., "Isolation, phenotype, and allostimulatory activity of mouse liver dendritic cells," *Transplantation 58*:848 (1994).

Berkner, K.L., "Expression of heterologous sequences in adenoviral vectors," *Curr. Top. Micro Immunol*, 158:39–66. (1992).

Inaba et al.,"Generation of large numbers of dendritic cells from mouse bone marrow cultures supplemented with granulocyte/macrophage colony–stimulating factor," *J. Exp. Med. 176*:1693–1702 (1992).

Horwitz, M.S., "Adenoviridae and Their Replication," in *Virology*, 2nd edition, Fields et al., eds., Raven Press, New York, 1990.

Billiar et al.,"An L–arginine–dependent mechanism mediates Kupffer cell inhibition of hepatocyte protein synthesis in vitro," *J. Exp. Med. 169*:1467–1472 (1989).

* cited by examiner

IL-4 DC
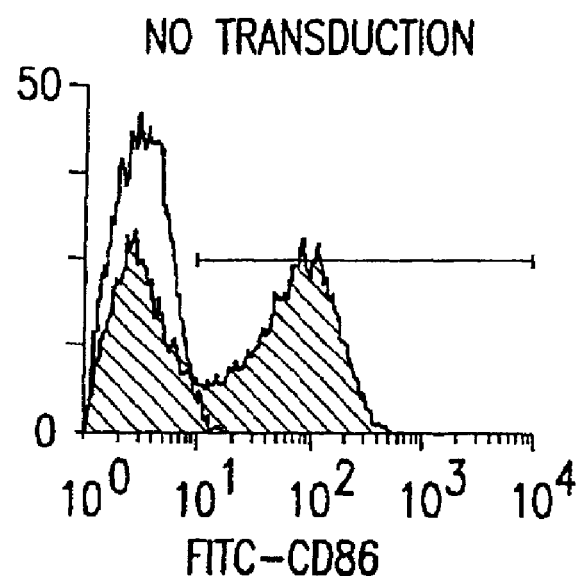
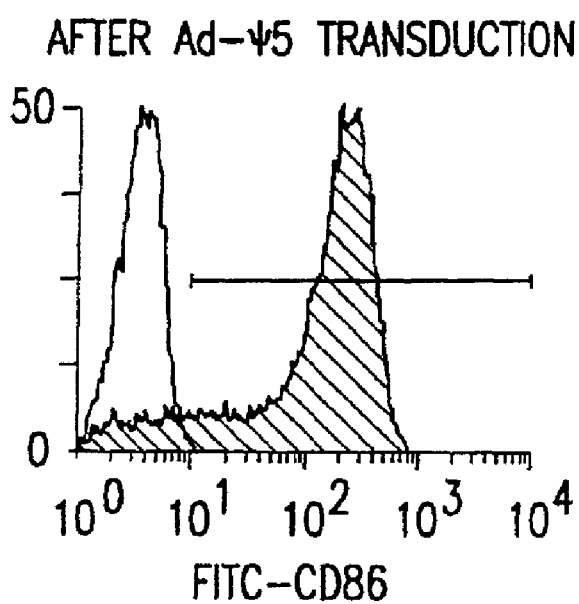
FIG.11A

TGFβ DC
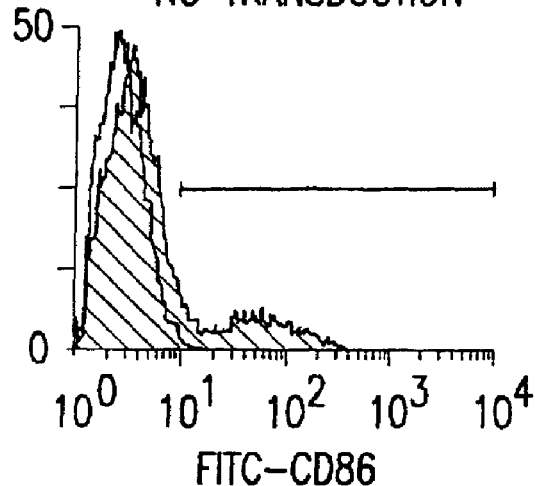
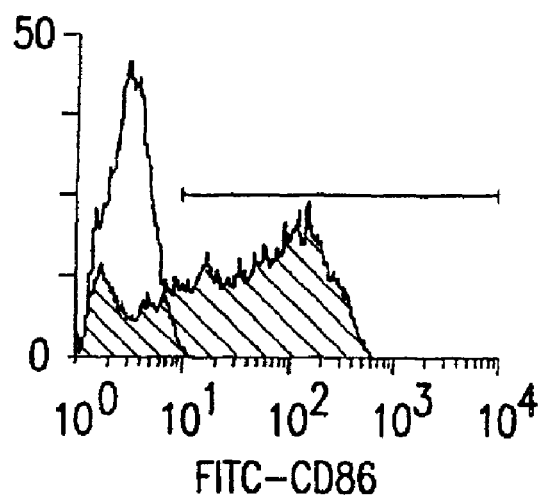
FIG. 11B

NF-κB ODN DC
NO TRANSDUCTION
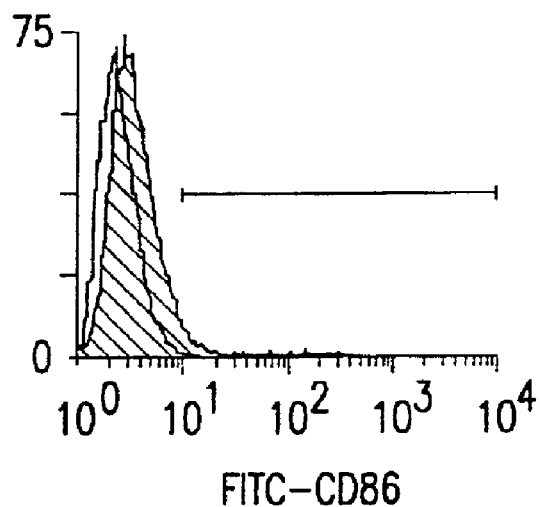
AFTER Ad-ψ5 TRANSDUCTION
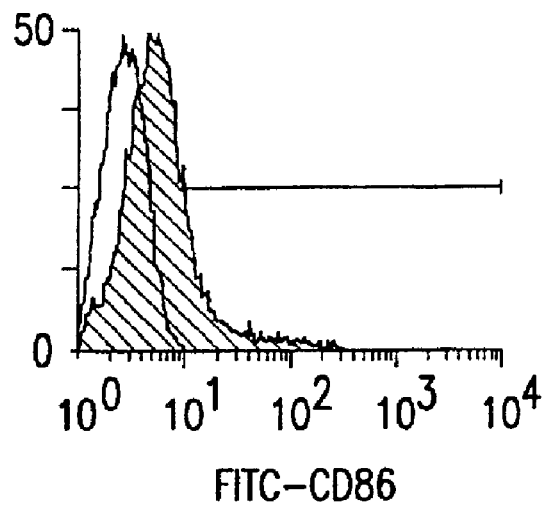
FIG.11C CTLA4Ig IS EFFICIENTLY PRODUCED BY
Ad-CTLA4Ig TRANSDUCED NF-κB ODN DC
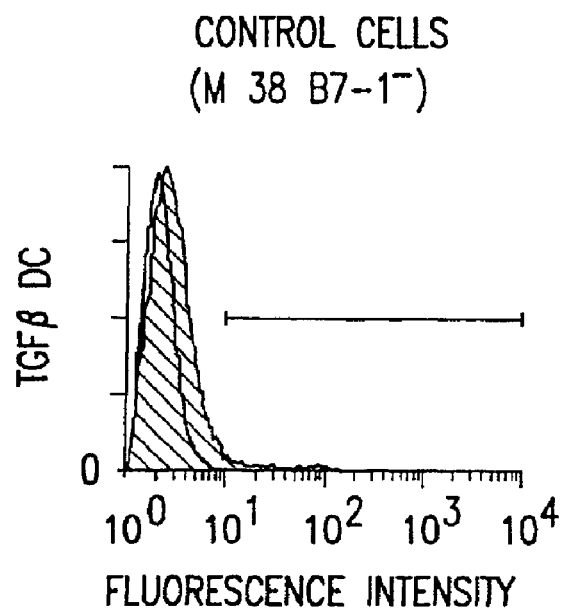
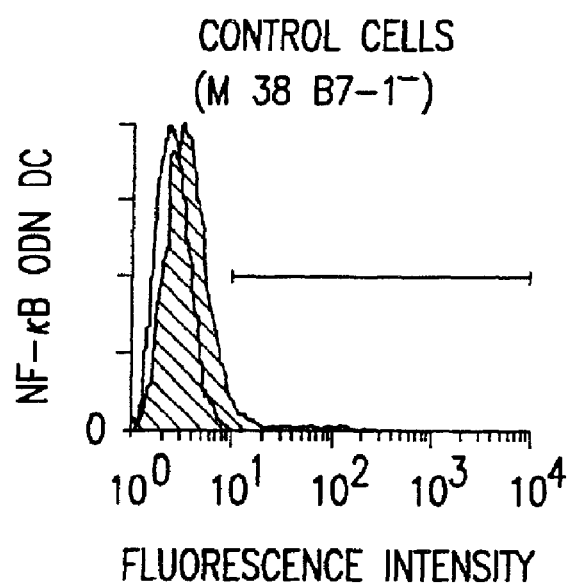
FIG.13A

CTLA4Ig IS EFFICIENTLY PRODUCED BY Ad-CTLA4Ig TRANSDUCED NF-κB ODN DC
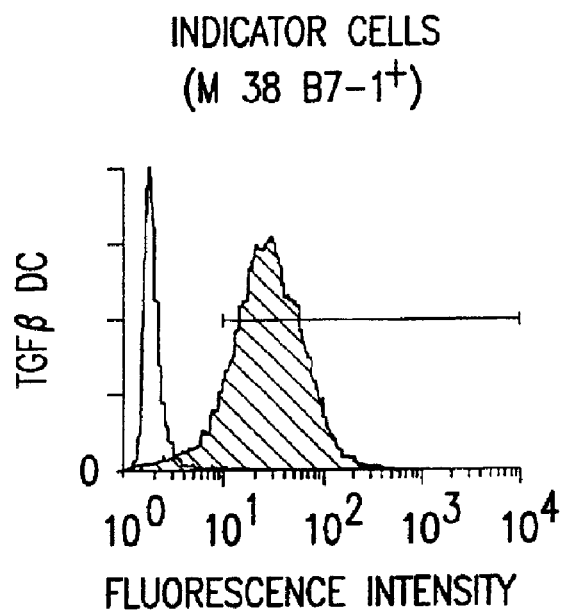
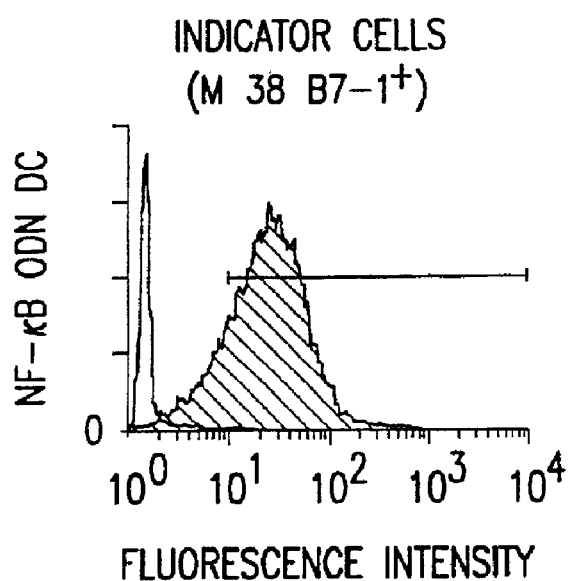
FIG.13B

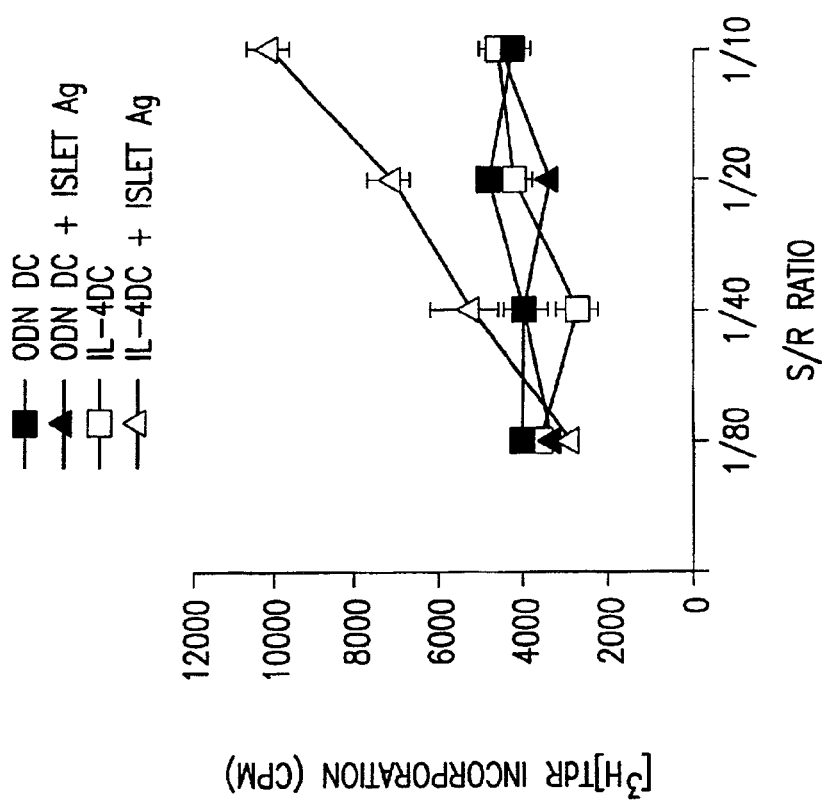

NOD BM DERIVED-IL4 DC, BUT NOT NFκB ODN DC, PULSED WITH ISLET LYSATE STRONGLY INDUCE T CELL PROLIFERATION
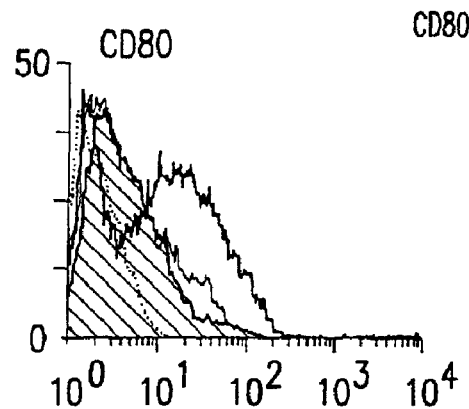
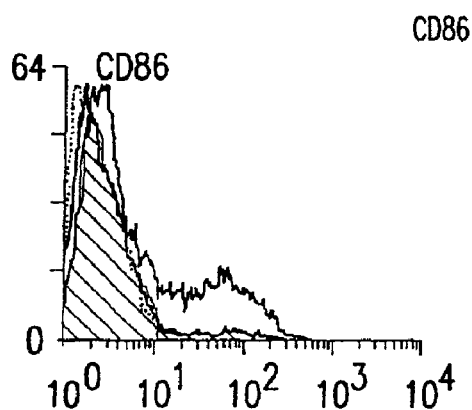
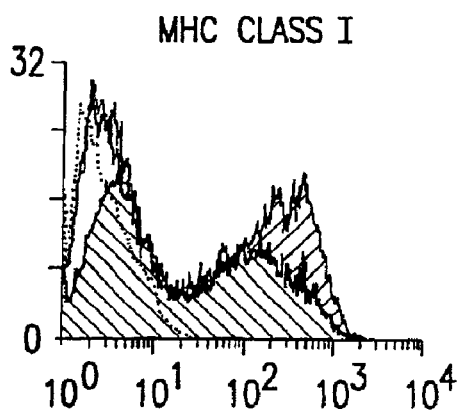
FIG. 15B

USE OF TOLEROGENIC DENDRITIC CELLS FOR ENHANCING TOLEROGENICITY IN A HOST AND METHODS FOR MAKING THE SAME

This application claims the benefit of provisional application Ser. No. 60/200,479 filed Apr. 28, 2000.

INTRODUCTION

The present invention relates to a method for regulating the immune response in a mammalian host wherein tolerogenic dentritic cells (DCs) are introduced into the mammalian host. The tolerogenic dentritic cells are obtained by harvesting dentritic cells from a mammalian donor and treating the cells with an oligodeoxyribonucleotide (ODN) which binds to nuclear factor κB (NF-κB). The tolerogenic dentritic cells are useful for prolonging graft survival in a mammalian host and for inhibiting the inflammatory response. The present invention also relates to tolerogenic DCs comprising a viral vector wherein the DCs maintain a tolerogenic state in the presence of the viral vector.

BACKGROUND OF INVENTION

Nuclear factor-κB (NF-κB) is a ubiquitous transcription factor that governs the expression of genes encoding cytokines, chemokines, growth factors, cell adhesion molecules and some acute phase proteins associated with various disease states. NF-κB is involved in immune and inflammatory reactions and its regulation contributes to a number of immunologically mediated diseases such as graft rejection, and diseases linked to inflammatory events such as autoimmune arthritis, asthma, septic shock, lung fibrosis, glomerulonephritis, artherosclerosis and AIDS.

DCs play a critical role in the initiation and regulation of immune responses and are instrumental in the induction and maintenance of tolerance (Banchereau and Steinman, *Nature* 392:245–252 (1998); Thomson and Lu, *Transplantation* 68:1–8 (1999)). DC activation is necessary for the role of DCs in the immune response and can be defined by two distinct processes, (1) maturation which involves the upregulation of MHC and costimulatory molecules, and (2) survival which involves the rescue of DCs from immediate apoptosis after the withdrawal of growth factors. See Rescigno et al., *J. Exp. Med.* 188:2175–2180 (1998). The mature DC expresses high levels of MHC class II and costimulatory molecules. In contrast, DCs with tolerogenic properties express low levels of costimulatory molecules and induce antigen-specific specific hyporesponsiveness by triggering T cell apoptosis. See Lu et al., *Transplantation* 60:1539–1545 (1995).

The inhibition of NF-κB can inhibit DC activation by blocking the maturation of DCs, a necessary process in DC activation. NF-κB is activated by a number of incoming signals from the cell surface. Once activated, NF-κB translocates into the nucleus and binds to the κB motif of the target gene. Nuclear translocation of NF-κB is associated with the expression of costimulatory molecules (e.g. CD40, CD86 and CD80) at the DC cell surface which correlates with the capacity of DCs to induce (or suppress) immune responses.

While DCs classically promote immune responses, they can be manipulated to induce antigen-specific hyporesponsiveness in vitro. The ability to manipulate the state of DC maturation in vitro has led to attempts to induce tolerance by administration of costimulatory molecule-deficient DCs in animal models of pancreatic islet cells or organ transplantation. See Fu et al., *Transplantation* 62:659–665 (1996); Rastellini et al., *Transplantation* 60:1366–1370 (1995); Lu et al., *Transplantation* 27:1808–1815 (1997); Gao et al., *Immunology* 98:159–170 (1999); Hirano et al., *Transplant Proc.* 32:260–264 (2000); Thomson and Lu, *Transplantation* 68:1–8 (1999). While these methods have had modest success, tolerance has not been achieved. This may be due to the late maturation/activation of DCs with upregulation of costimulatory molecules upon encountering a host microenvironment rich in pro-inflammatory mediators. The ability to manipulate the state of DC maturation may also be useful for the treatment of other diseases involving inflammatory events, such as autoimmune arthritis, asthma, septic shock, lung fibrosis, glomerulonephritis, artherosclerosis and AIDS.

U.S. Pat. No. 5,871,728 of Thomson et al., discloses a method for enhancing tolerogenicity to a foreign graft in a host mammal comprising propagating immature DCs from a mammalian source, culturing the immature DCs in the presence of a cytokine and administering the propagated immature DCs to the host. However, DCs cultured according to the method of U.S. Pat. No. 5,871,728, in which immature DCs are cultured in the presence of a cytokine alone, are likely to mature after encountering a host microenvironment. In fact, U.S. Pat. No. 5,871,728 also discloses a method for culturing mature immunostimulatory DCs which differs from the method of culturing immature DCs only by the addition of an extracellular matrix protein together with the cytokine. The inventors of the U.S. Pat. No. 5,871,728 patent acknowledge that the addition of the extracellular matrix protein during culturing creates an environment similar to that of the microenvironment in the host and thus leads to the maturation of the DCs. Therefore, it is very likely that the immature DCs of U.S. Pat. No. 5,871,728 will mature when introduced into a host cell microenvironment.

Genetic engineering of DCs to express immunosuppressive molecules has also been considered an attractive approach to alleviating of foreign graft rejection and autoimmune disorders. See Lu et al., *J. Leukoc. Biol.* 66:293–296 (1999). Adenoviral delivery of cytotoxic T lymphocyte antigen 4-immunoglobulin (CTLA4Ig) into DCs has been shown to promote DCs in vitro tolerogenicity and survival in allogeneic recipients. Lu et al., *Gene Ther.* 6:554–563 (1999). In addition, delivery of transforming growth factor-β (TGF-β) using an adenoviral vector prevents the reduction of DCs generally seen with adenovirus infection and also increases the numbers and prolongs the survival of the infected DCs in the spleen of a host to whom the DCs are administered. Lee et al., *Transplantation* 66:1810–1817 (1998).

Efforts have been made to develop genetic immunization with DCs infected with a viral vector expressing a gene of interest. Tuting et al. (*J. Gene Med.* 1:400–406 (1999)) have shown that DCs infected with a recombinant adenovirus encoding tyrosinase-related protein-2 (TRP2) induces antimelanoma immunity. In addition, DCs have also been used for developing vaccinations against Epstein bar virus (EBV) by infecting DCs with an adenoviral vector encoding EBV antigens. Ranieri et al., *J. Virol.* 73:10416–10425 (1999).

While modification of DCs may be an attractive approach to the therapy of foreign graft rejection and autoimmune disorders, there are potential problems associated with such an approach. As noted above, tolerogenicity may be enhanced in a host by the administration of immature DCs which are hyporesponsive. However, infection of DCs with an adenoviral vector alone stimulates maturation of DCs and enhances the immunostimulatory capacity of DCs. See Rea et al., *J. Virol.* 73:10245–10253 (1999). In addition, it has been shown that infection of DCs with an adenovirus expressing eGFP enhanced costimulatory molecule expression and induction of CTL responses of both TGF-β and IL-4 in a dose dependent manner. See Lu et al., *J. Leukocyte Bio.* Supplement 2, abstract # B52 (1998).

Therefore, there is a need for a method for producing tolerogenic DCs which do not readily mature when introduced into a host. In addition, there is a need for a method of enhancing tolerogenicity in a host (such as autoimmune disease) using tolerogenic DCs wherein the tolerogenic DCs do not readily mature when introduced in the host microenvironment. Furthermore, there is a need for a method of producing tolerogenic DCs comprising a viral vector wherein said DCs maintain their tolerogenicity in the presence of the viral vector.

SUMMARY OF THE INVENTION

The present invention relates to tolerogenic mammalian dendritic cells (DCs) and methods for the production of the tolerogenic DCs. In addition, the present invention provides a method for enhancing tolerogenicity in a host comprising administering the tolerogenic mammalian DCs of the present invention to the host. Enhanced tolerogenicity in a host is useful for prolonging foreign graft survival and for ameliorating inflammatory related diseases, such as autoimmune diseases.

The present invention also provides a method of producing tolerogenic DCs comprising a viral vector wherein the DCs maintain their tolerogenicity in the presence of the viral vector. The viral vector-comprising tolerogenic DCs of the present invention may improve foreign graft survival and may be useful for ameliorating of inflammatory related diseases, such as autoimmune diseases. The viral-vector-comprising tolerogenic DCs of the present invention may express factors useful for foreign graft survival and for the treatment of inflammatory related diseases.

In one aspect of the invention, the tolerogenic mammalian DCs comprise an oligodeoxynucleotide (ODN) which has at least one NF-κB binding site. In a preferred embodiment, the tolerogenic DCs of the present invention comprise an ODN which has two NF-κB binding sites. Tolerogenic DCs of the present invention, which comprise an ODN having NF-κB binding sites, can be cultured in a tolerogenic state in vitro and do not readily mature in vivo.

The present invention provides a method for producing tolerogenic mammalian DCs. The method comprises propagating immature mammalian DCs from a mammalian donor, incubating the DCs with an ODN having at least one NF-κB binding site under conditions wherein the DCs internalize the ODN and culturing said DCs. The DCs are cultured in the presence of at least one cytokine, such as GM-CSF, and may also be cultured in the presence of TGF-β, e.g. TGF-β1.

The present invention further provides a method for enhancing tolerogenicity in a host comprising propagating immature mammalian DCs from a mammalian donor, incubating said DCs with an ODN which has at least one NF-κB binding site under conditions wherein the DCs internalize the ODN, culturing the ODN-comprising DCs and administering the ODN-comprising DCs to the mammalian host in an effective amount to enhance tolerogenicity in the host.

In addition, the present invention provides a method for producing viral vector-comprising tolerogenic DCs comprising propagating immature mammalian DCs from a mammalian donor, incubating the DCs with an ODN having at least one NF-κB binding site under conditions wherein the DCs internalize the ODN, culturing said DCs and infecting said DCs with a viral vector. The viral vector may encode factors useful for prolonging foreign graft survival and for treating autoimmune diseases.

DESCRIPTION OF THE DRAWINGS

FIG. 11 is a flow cytometric analysis showing the ability of NF-κB ODN to block adenoviral induced DC maturation. (A) shows the effect of the presence of IL-4, TGF-β NF-κB ODN on DC maturation. (B) shows that after adenovirus transduction, DCs expressing IL-4 and TGF-β mature, whereas DCs expressing NF-κB ODN do not.

FIG. 13 is a fluorescence analysis showing that NF-κB does not interfere with adenoviral CTLA4 Ig transgene expression.

FIG. 15 is a graph showing that the immunostimulatory capacity of DC from NOD mice is significantly inhibited by NF-κ ODN.

DETAILED DESCRIPTION

Figure 1:
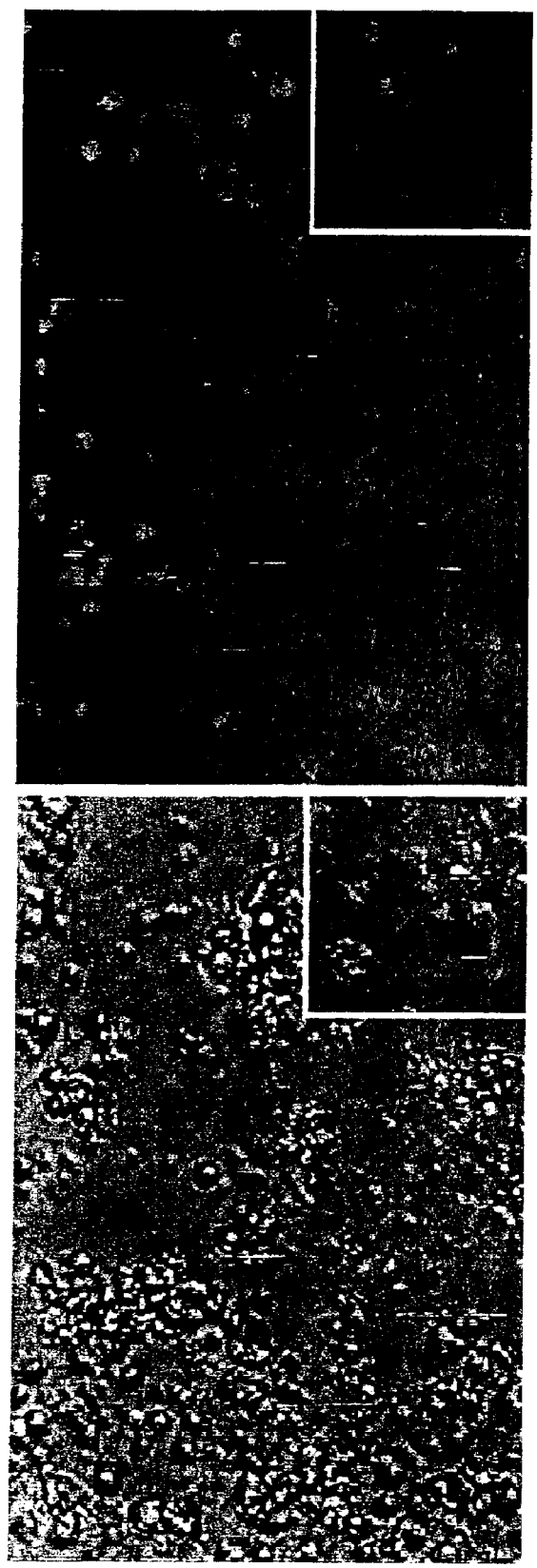
FIG. 1 shows the efficient incorporation and persistence of NF-κB ODN in DCs. Left Panel: phase contrast microscopy of DCs comprising FITC-conjugated NF-κB ODN. A typical DC morphology is shown in the inset in the left panel. Right Panel: fluorescence microscopy of the same DCs as the right panel after an 18 hour pulse with FITC-NF-κB ODN. The inset shows the same cells as the inset of the left panel. Magnification=40×, inset=100×.

The present invention relates to the ability to manipulate the activation/maturation state of DCs to produce tolerogenic DCs and is based in part on the discovery that an oligodeoxynucleotide (ODN) having one or more nuclear factor-κB (NF-κB) binding sites can impart tolerogenicity to immature dendritic cells (DCs). The present invention provides tolerogenic DCs which comprise an ODN having at least one NF-κB binding site and methods for their production. The tolerogenic DCs of the present invention enhance tolerance in a mammalian host are useful for prolonging foreign graft survival in a mammalian host and for ameliorating inflammatory-related diseases, such as autoimmune diseases, including, but not limited to, autoimmune arthritis, autoimmune diabetes, asthma, septic shock, lung fibrosis, glomerulonephritis, artherosclerosis, as well as AIDS.

The present invention further provides viral vector-comprising tolerogenic DCs which comprise an ODN having one or more NF-κB binding sites and methods for their production. The viral vector-comprising tolerogenic DCs of the present invention enhance tolerance in a host and are useful for prolonging foreign graft survival in said host and for ameliorating inflammatory-related diseases, such as autoimmune diseases, including, but not limited to, autoimmune arthritis, autoimmune diabetes, asthma, septic shock, lung fibrosis, glomerulonephritis, artherosclerosis, as well as AIDS.

5' AGGGACTTTCCGCTGGGGACTTTCC 3' (SEQ ID NO:1), wherein the NF-κB binding sites are underlined and indicated in bold-face.

The introduction of NF-κB ODN to DCs to produce the tolerogenic DCs of the present invention can prevent the activation/maturation of the DCs. See Example 2–5 and Example 9 and FIGS. 2–5, 10–14. In addition, the introduction of NF-κB ODN to DCs to produce the tolerogenic DCs of the present invention can inhibit the allostimulatory capacity of DCs. See Example 5 below and FIG. 5. The NF-κB ODN can act as a decoy in DCs to specifically inhibit the DNA binding of NF-κB because the NF-κB ODN can specifically bind NF-κB in DCs. See Example 6 below and FIG. 6. Furthermore, NF-κB decoys can interfere with the NF-κB-dependent transcription in DCs. See Example 7 below and FIG. 7.

The tolerogenic and viral vector-comprising tolerogenic DCs of the present invention may be propagated in the presence of an ODN containing at least one NF-κB binding site alone or in the presence of an ODN containing at least one NF-κB binding site and at least one cytokine (e.g. granulocyte-macrophage colony-stimulating factor (GM-CSF)). In a preferred embodiment, the tolerogenic and viral vector-comprising tolerogenic DCs of the present invention are propagated in the presence of an ODN having SEQ ID NO:1, GM-CSF and TGF-β1.

As stated above, the NF-κB-treated DCs of the present invention are tolerogenic. In addition, the NF-κB DCs of the present invention maintain their tolerogenicity As used herein, a foreign graft specimen is a graft specimen from a source other than the host mammal, e.g. a donor source. The graft specimens of the present invention may be either homografts (or allografts) which are from the same species as the host, or the graft specimens may be xenografts which are from a species different from the host.

The tolerogenic DCs and viral vector-comprising DCs of the present invention are derived from mammalian DCs, obtained from donor mammals of the same or different species or from an autologus source (i.e. they are from the host). In a preferred embodiment, where the tolerogenic and viral vector-comprising DCs of the present invention are used to prolong foreign graft survival, the DCs are derived from either an autologous or donor source. In another preferred embodiment, where the tolerogenic and viral vector-comprising DCs of the present invention are used for ameliorating of inflammatory related diseases, such as autoimmune diseases, the DCs are derived from an autologous source.

The tissues from which DCs may be isolated to produce the tolerogenic and viral vector-comprising tolerogenic DCs of the present invention include, but are not limited to, liver, spleen, bone marrow, peripheral blood, thymus or lymph nodes. In a preferred embodiment, the source of the DCs is bone marrow.

The tolerogenic and viral vector-comprising tolerogenic DCs of the present invention are treated with an ODN which has one or more binding sites for NF-κB. In a preferred embodiment, the ODN has two NF-κB binding sites. In a particular preferred embodiment, the ODN is double-stranded and has the following nucleotide sequence: when infected with a viral vector, and particularly when infected with an adenoviral vector. See Example 9 and FIGS. 10–14. Generally, adenovirus infection up-regulates costimulatory molecule expression in DCs. However, the tolerogenic DCs of the present invention, comprising an ODN containing at least one NF-κB binding site prevent the up-regulation of costimulatory molecules by adenovirus.

To produce the viral vector-comprising tolerogenic DCs of the present invention, the DCs are infected with a viral vector after treatment with the ODN containing at least one NF-κB binding site. The viral vectors can be derived from the following nonlimiting virus types: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corciciviridae; Group Cryptic virus; group Cryptovirus; Cucumovirus virus group Family Φ6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdovindae; Group Rhizidiovirus; Siphoviridae; Sobemovirus group; SSV1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; Plant virus satellites.

In one embodiment of the invention, the viral vector is derived from retrovirus, adenovirus, adeno-associated virus (AAV), or herpes simplex virus (HSV). In a preferred embodiment of the invention, the viral vector is derived from adenovirus. Adenovirus is a non-enveloped, nuclear DNA virus with a genome of about 36 kb. See generally, Horwitz, M. S., "Adenoviridae and Their Replication," in *Virology*, 2nd edition, Fields et al., eds., Raven Press, New York, 1990. Recombinant adenoviruses have advantages for use as expression systems for nucleic acid molecules coding for, inter alia, proteins, ribozymes, RNAs, antisense RNA that are foreign to the adenovirus carrier (i.e. a transgene), including tropism for both dividing and non-dividing cells, minimal pathogenic potential, ability to replicate to high titer for preparation of vector stocks, and the potential to carry large inserts. See Berkner, K. L., 1992, *Curr. Top. Micro Immunol*, 158:39–66; Jolly D., 1994, *Cancer Gene Therapy*, 1:51–64.

The adenoviral vector may be derived from adenovirus serotype 2 (Ad 2) or serotype 5 (AD5) and has a substantially deleted E1 and E3 region. Other adenovirus serotypes can also be used as backbones for the adenoviral vector including, inter alia, Ad 6, Ad 9, Ad 12, Ad 15, Ad 17, Ad 19, Ad 20, Ad 22, Ad 26, Ad 27, Ad 28, Ad 30 and A 39. From these enumerated adenovirus serotypes, Ad 2 and Ad 5are preferred.

The viral vector may comprise a transgene. As set forth above, a transgene is a nucleic acid molecule that codes for, inter alia, a protein, RNA, ribozyme, antisense RNA to be expressed into target cell. Nonlimiting examples of transgenes include TGF-β, IL10, CTLA4-Ig, sCD40-Ig, IL-4, IL-13, FasL, IRAP, VIL-10, sICAM-1, sICAM-3 and TRAIL. The tolerogenic viral-infected DCs of the present invention can prolong foreign graft survival (see Example 8 and Table 1 below, and FIG. 8) in a host and/or treat inflammatory related diseases, such as autoimmune diseases (e.g. Type 1 diabetes; see Example 10 and FIGS. 15–16).

The present invention provides for a method of producing tolerogenic DCs comprising (a) propagating immature mammalian DCs from a mammalian donor, (b) incubating the DCs with an ODN having at least one NF-κB binding site under conditions wherein the DCs internalize the ODN, and (c) culturing said DCs. In one embodiment, the ODN has two NF-κB binding sites. In a particularly preferred embodiment, the ODN has the nucleotide sequence set forth by SEQ ID NO:1. The method may further comprise incubating the DCs in the presence of one or more cytokines, preferably GM-CSF in the presence or absence of TGF-β (e.g. TGF-β1) prior to or at the same as the incubation with an ODN containing at least one NF-κB binding site.

Isolating and propagating the mammalian DCs may be accomplished by any technique known to the skilled artisan. See, e.g., Inaba et al., *J. Exp. Med.* 176:1693–1702 (1992); Lu et al., *Transplantation* 60:1539–1545 (1995); and Lu et al., *Transplantation* 64:1808–1815 (1997); Woo et al., *Transplantation* 58:848 (1994), all incorporated herein by reference. For example, the mammalian DCs may be generated from precursors, isolated from a donor, in accordance with the method described in Example 1 below. Those skilled in the art would be able to implement modifications to the disclosed method in Example 1 for propagating DCs without the exercise of undue experimentation.

Once generated, the mammalian DCs may be propagated by any suitable cell culturing technique known to the skilled artisan. For example, the DCs may be propagated in accordance with the method in Example 1 below. See Inaba et al., *J. Exp. Med.* 176:1693–1702 (1992); Lu et al., *Transplantation* 60:1539–1545 (1995); and Lu et al., *Transplantation* 64:1808–1815 (1997), all incorporated herein by reference The present invention also provides a method for producing viral vector-comprising tolerogenic DCs which comprises (a) propagating immature mammalian DCs from a mammalian donor, (b) incubating the DCs with an ODN having at least one NF-κB binding site under conditions wherein the DCs internalize the ODN, (c) culturing said DCs, and (d) infecting said DCs with a viral vector. In one embodiment, the ODN has two NF-κB binding sites. In a particularly preferred embodiment, the ODN has the nucleotide sequence set forth by SEQ ID NO:1. The method may further comprise incubating the DCs in the presence of one or more cytokines, preferably GM-CSF and in the presence or absence of TGF-β (e.g. TGF-β1) prior to or at the same as the incubation with an ODN containing at least one NF-κB binding site. The viral vector is preferably derived from adenovirus and may comprise a transgene. The transgene may encode, inter alia, TGFβ, IL10, CTLA4, SCD40-Ig, IL-4, IL-13, FasL, IRAP, VIL-10, sICAM-1, sICAM-3 and TRAIL.

The present invention further provides a method for enhancing tolerogenicity in a host comprising (a) propagating immature mammalian DCs from a donor, (b) incubating said DCs with an ODN which has at least one NF-κB binding site under conditions wherein the DCs internalize the ODN, (c) culturing the ODN-comprising DCs, and (d) administering the ODN-comprising DCs to the mammalian host in an effective amount. In one embodiment, the ODN has two NF-κB binding sites. In a particularly preferred embodiment, the ODN has the nucleotide sequence set forth by SEQ ID NO:1. The method may further comprise incubating the DCs in the presence of one or more cytokines, preferably GM-CSF and in the presence or absence of TGF-β (e.g. TGF-β1) prior to or at the same as the incubation with an ODN containing at least one NF-κB binding site.

Tacrolimus (FK 506) can prolong graft survival which is improved when FK 506 is administered to the host together with dendritic cells. See Khanna et al., *Transplantation* 65:479–485 (1998), incorporated herein by reference. In addition, cyclosporine A (CSA) inhibits the expression of costimulatory molecules in vivo on dendritic cells. See Lee et al., *Transplantation* 68:1255–1263 (1999), incorporated herein by reference. Therefore, the present invention, the method for enhancing tolerogenicity in a host, as described above, may further comprise administering the tolerogenic DCs of the present invention together with FK 506 and/or cyclosporine A (CSA) to the mammalian host.

In another embodiment, the method may further comprise infecting the DCs with a viral vector wherein the DCs maintain their tolerogenicity. See Example 9 below and FIGS. 10–14. The viral vector is preferably derived from adenovirus and may comprise a transgene. The transgene may encode, inter alia, TGFβ, IL10, CTLA4, SCD40-Ig, IL-4, IL-13, KasL, IRAP, VIL-10, sICAM-1, sICAM-3 and TRAIL. The method is useful for prolonging foreign graft survival (see Example 8 and Table 1 below) in a host and for treating a host with an inflammatory related disease, such as an autoimmune disease (e.g. Type 1 diabetes; see Example 10 below and FIGS. 15–16).

Tacrolimus (FK 506) can prolong graft survival which is improved when FK 506 is administered to the host together with dendritic cells. See Khanna et al., *Transplantation* 65:479–485 (1998), incorporated herein by reference. In addition, cyclosporine A (CSA) inhibits the expression of costimulatory molecules in vivo on dendritic cells. See Lee et al., *Transplantation* 68:1255–1263 (1999), incorporated herein by reference. Therefore, the present invention, the method for enhancing tolerogenicity in a host, as described above, may further comprise administering the tolerogenic and viral vector-infected tolerogenic DCs of the present invention together with FK 506 and/or cyclosporine A (CSA) to the mammalian host.

In another aspect, the invention relates to a kit for use in enhancing tolerogenicity in a host comprising the tolerogenic or viral vector-comprising tolerogenic DCs of the present invention. The DCs may be isolated in accordance with the methods described herein. The kit may contain cells in culture; cells frozen in media+a cryoprotectant, such as dimethyl sulfoxide (DMSO); or lyophilized cells. Alternatively, the kit may comprise reagents necessary to produce tolerogenic DCs. For example the kit may comprise reagents for isolating precursors from a host, reagents for generating DCs from the precursors, reagents for propagating the DCs, such as at least one cytokine (e.g. GM-CSF), TGF-β and reagents necessary to enhance the tolerogenicity of the of the DCs (e.g. an ODN containing at least one NF-κB binding site). The kit may comprise any variation of the reagents necessary to produce tolerogenic DCs. The kit may additionally comprise a protocol for the administration of the DCs of the present invention, a physiologically acceptable carrier, immunosuppressive agents, etc. The kit may further comprise diagnostic reagents to determine the therapeutic effectiveness of the DCs after administration.

The kit may be used to prolong foreign graft survival in a transplant host or to treat an inflammatory related disease in a host.

Means of administering the tolerogenic and viral vector-comprising tolerogenic DCs of the present invention to a mammalian host include, but are not limited to, conventional and physiologically acceptable routes, such as, for example, oral, pulmonary, parenteral (intramuscular, intra-articular, intraperitoneal, intravenous (IV) or subcutaneous injection), inhalation (via a fine powder formulation or a fine mist, aerosol), transdermal, intradermal, nasal, vaginal, rectal, or sublingual routes of administration. The tolerogenic and viral vector-comprising tolerogenic DCs are preferably administered intravenously or subcutaneously.

The tolerogenic and viral vector-comprising tolerogenic DCs of the present invention may be administered with a carrier. Such carriers comprise any suitable physiological solution or dispersant or the like. The physiological solutions comprise any acceptable solution or dispersion media, such as saline or buffered saline. The carrier may also comprise antibacterial and antifungal agents, isotonic and adsorption delaying agents, and the like. Except insofar as any conventional media, carrier or agent is incompatible with the active ingredient, its use in the compositions is contemplated. The carrier may further comprise one or more immunosuppressive agents in dosage unit form. Examples of immunosuppressive agents include, but are not limited to, cytokines, such as, for example, interleukin-10 (IL-10) and TGF-β. In addition, the carrier may also comprise pharmaceuticals such as, for example cyclosporine A and tacrolimus (FK 506).

Dosage of the tolerogenic and viral vector-comprising tolerogenic DCs of the present invention to be administered in vivo is determined with reference to various parameters, including the species of the host, the age, weight and disease status. Dosage also depends upon the location to be targeted within the host, e.g. foreign graft transplantation site or joints of an arthritic host. For example, direct targeting of joints may require different dosages than administration into the blood stream of a mammalian host. The dosage is preferably chosen so that administration causes an effective result, as measured by molecular assays, prolongation of foreign graft survival, and alleviation of an inflammatory disease. Dosages may range from $1 \times 10^4$ DC to $1 \times 10^9$ DC per administration. In one embodiment, the dosage ranges from $5 \times 10^5$ DC to $5 \times 10^7$ DC. To achieve maximal therapeutic effect, several doses may be required.

Where the tolerogenic and viral vector-comprising tolerogenic DCs of the present invention are to be used for the prolongation of foreign graft survival, administration of the DCs into the mammalian host may be conducted prior to transplantation with the foreign graft. More particularly, administration may be conducted one week prior to transplantation. Prior administration has a prophylactic effect. Administration may also be conducted at the time of the transplant and up to one-two weeks after the transplant to ensure acceptance of the foreign graft.

Immunosuppressive agents, such as those listed above, may be administered to a host at the time of foreign graft transplantation and may be administered daily thereafter for a period of time necessary to optimize graft survival. Practitioners will know to adjust the administration of immunosuppressive agents. The amount of immunosuppressive agents necessary may change due to the therapeutic effect of the tolerogenic and viral vector-comprising tolerogenic DCs of the present invention as well as the host response to the transplantation.

To determine appropriate times for administering the tolerogenic and viral vector-comprising tolerogenic DCs of the present invention, a skilled artisan may employ conventional clinical and laboratory means for monitoring graft survival, graft function and the host's reaction to the transplant. Biochemical and immunological tests may be used for such monitoring.

Where the tolerogenic and viral vector-comprising tolerogenic DCs of the present invention are to be used for the alleviation of an inflammatory related disease, administration may be conducted daily, weekly, monthly or yearly depending on the alleviation of the symptoms of the disease. Administration can continue as long as necessary to alleviate the disease.

The tolerogenic and viral vector-comprising tolerogenic DCs of the present invention do not have to be derived from the same species as the host to be treated, although as mentioned above, they may be from the same species from a donor or from the host itself. For instance, DCs may be isolated from a baboon donor to produce the tolerogenic and viral vector-comprising tolerogenic DCs of the present invention and may be administered into a human host to enhance tolerogenicity therein. See, e.g., Starzl, et al., *Immunological Reviews* 141:213 (1994), the contents of which are incorporated herein by reference.

The invention is further illustrated by the following nonlimiting examples, which are not intended to limit the scope of the invention.

EXAMPLES

Example 1

DCs Effectively Incorporate NF-κB ODN

A Materials and Methods

Oligodeoxyribonucleotides (ODN): Double-stranded ODN decoys having two NF-κB binding sites were generated using equimolar amounts of single-stranded sense and antisense phosphorothioate-modified oligonucleotides containing two NF-κB binding sites as described by Bielinska et al., *Science* 250:997–1000 (1990) (designated NF-κB-ODN):

Sense oligonucleotide sequence with NF-κB binding sites in bold-faced type and underlined:

5' AGGGACTTTCCGCTGGGGACTTTCC 3' (SEQ ID NO:1).

Antisense oligonucleotide sequence with NF-κB binding sites in bold-faced type and underlined:

5' GGAAAGTCCCCAGCGGAAAGTCCCT 3' (SEQ ID NO:2).

As a control for non-specific sequence effects as well as aptameric effects that might have been induced by the GGGG quartet in the specific decoy, a double-stranded oligonucleotide consisting of a random sequence was used and designated ODN1 herein Sense oligonucleotide sequence for ODN1:

5' ACCAGTCCCTAGCTACCAGTCCCTA 3' (SEQ ID NO:3).

Antisense oligonucleotide sequence for ODN1:

5' TAGGGACTGGTAGCTAGGGACTGGT 5' (SEQ ID NO:4).

In addition, a control sequence designated ODN2 herein containing an incomplete NF-κB consensus sequence was used:

Sense oligonucleotide sequence of ODN2 with incomplete NF-κB sites designated in bold-faced type and underlined:

5' AGGTACTGTCCGCGTTAGACGTGCC 3' (SEQ ID NO:5).

Antisense oligonucleotide sequence of ODN2 with incomplete NF-κB sites designated in bold-faced type and underlined:

5' GGCACGTCTAACGCGGACAGTACCT 3' (SEQ ID NO:6).

Sense and antisense strands of each oligonucleotide were mixed in the presence of 150 mM NaCl, heated to 100° C. and allowed to cool to room temperature to obtain double-stranded DNA. FITC-conjugated double-stranded decoys were prepared in a similar fashion.

Animals: Male C57BL/10J (B10; H2b; Iab) and C3H/HeJ (C3H; H2k; Iak; Iek) mice and Female NOD mice were purchased from Jackson Laboratory (Bar Harbor, Me.), and maintained in a specific pathogen-free facility. Animals were fed standard chow ad libitum and used at 8–12 weeks of age.

Cell Culture: Bone marrow (BM) cells were harvested from femurs of normal B10 or NOD mice and were cultured in 24 well plates ($2\times10^6$ per well) in 2 ml of RPMI-1640 media (Life Technologies, Gaithersburg, Md.) supplemented with antibiotics and 10% fetal calf serum (FCS). 4 ng/ml recombinant mouse granulocyte-macrophage colony-stimulating factor (GM-CSF) (Schering-Plough, Kenilworth, N.J.) was added to propagate immature DCs. In addition to GM-CSF, 1000 units/ml recombinant IL-4 (Schering-Plough, Kenilworth, N.J.) was added at the initiation of culture of the DCs. DCs were generated by a procedure modified from procedures previously described. See Inaba et al., *J. Exp. Med.* 176:1693–1702 (1992); Lu et al., *Transplantation* 60:1539–1545 (1995); and Lu et al., *Transplantation* 64:1808–1815 (1997), all incorporated herein by reference. Cytokine-enriched medium was refreshed every 2 days; after gentle swirling of the plates, half of the old medium was aspirated and an equivalent volume of fresh, cytokine-supplemented medium was added as well as IL-4. Thus, nonadherent granulocytes were depleted without dislodging clusters of developing DCs attached loosely to a monolayer of plastic adherent-macrophages. Nonadherent cells released spontaneously from the clusters and were harvested after 5–7 days.

B. Results

To demonstrate that DCs can take up double-stranded ODN efficiently, mouse bone marrow (BM)-derived DCs propagated in GM-CSF+IL-4 (IL-4 DC) for 4–5 days were exposed to FITC-conjugated NF-κB ODN for time periods ranging from 2–36 hours. As shown in FIG. 1, the majority of DCs (>80%) exhibited fluorescence, indicating the presence of NF-κB ODN. Intracellular ODN could be detected for at least 14 days in culture. During this time, DCs remained viable without evidence of toxicity. Uptake could be detected as early as 2 hours after incubation, with peak fluorescence noted after an 18 hour exposure of the DCs to NF-κB ODN. DCs cultured with GM-CSF+IL-4 for 6–7 days develop to fully mature cells that lose their phagocytic capacity. When fully mature DCs ($CD40^+$, $CD80^+$, $CD86^+$, MHC class $I^+$ and MHC class $II^+$) were exposed to NF-κB ODN, no fluorescence could be observed in the cells indicating an inability to take up the FITC-conjugated oligonucleotide, consistent with the inability of these cells to process exogenous antigen.

Example 2

NF-κB ODN Prevent DC Activation In Vitro

A. Materials and Methods

Nitric oxide production in cultures was determined by the Greiss reaction, a colorimetric assay for the stable end product, nitrite ($NO_2^-$). See Billiar et al., *J. Exp. Med.* 169:1467–1472 (1989), incorporated herein by reference. 100 μl aliquots of supernatant were mixed with an equal volume of Greiss reagent (1% sulfanilamide, 0.1% napthylethylene diamine dihydrochloride, 2.5% $H_3PO_4$) and incubated at room temperature for 10 minutes. Absorbence at 570 nm was measured in an automated counter and compared to a standard curve generated using $NaNO_2$. Experiments were performed in triplicate on two separate occasions.

B. Results

Figure 2:
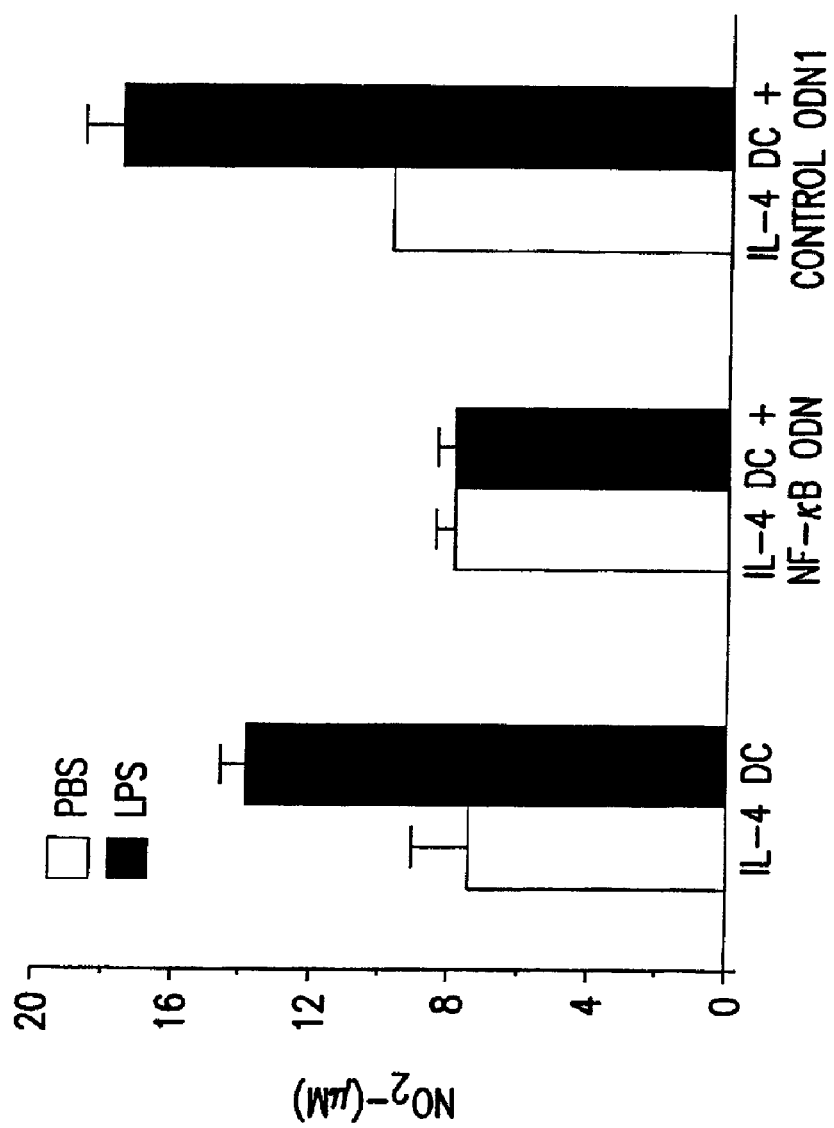
FIG. 2 is a bar graph showing the inhibition of nitric oxide production by NF-κB ODN DCs in response to LPS stimulation. Nitrite levels in the culture supernatant of $2 \times 10^5$/ml IL-4 DC, NF-κB ODN DCs, or control ODN1 DCs stimulated by 10 μg/ml LPS for 18 hr.
Figure 3A:
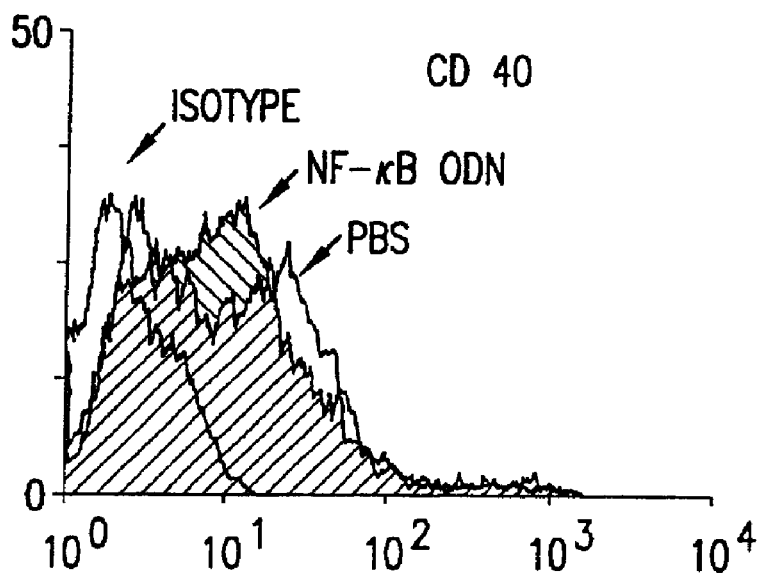
FIG. 3 represents a flow cytometric analysis showing the inhibition of costimulatory molecule expression in NF-κB ODN DCs. DCs were isolated from B10 (H2b, IAb) bone marrow and were propagated with GM-CSF+IL4. The DCs were then cultured in the presence of either NF-κB ODN or control ODN1. Panels show the expression of CD40, CD80, CD86, MHC class I, class II and the DC differentiation marker CD11c. Open profiles denote Ig isotype controls. CD86 and, to a lesser extent, CD80 surface molecule expression was impaired by NF-κB ODN. Surface molecule expression was not affected by culturing the DCs in the presence of PBS or control ODN1.
Figure 3B:
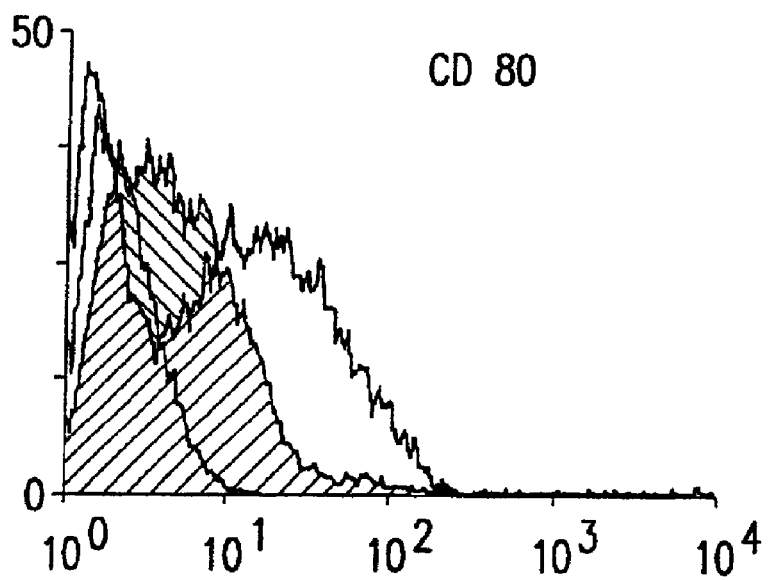
Figure 3C:
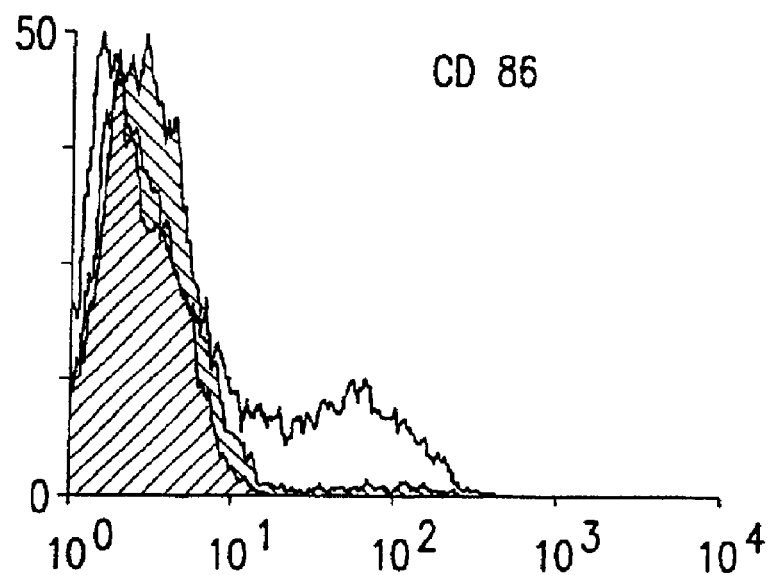
Figure 3D:
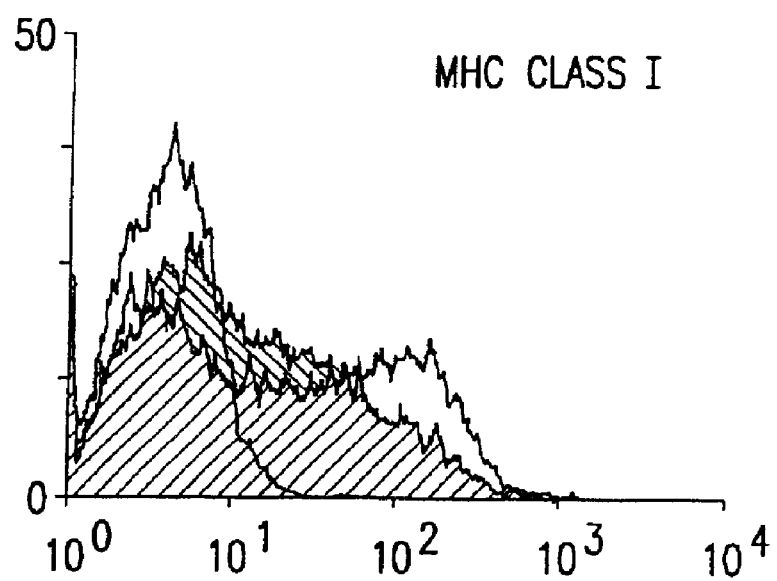
Figure 3E:
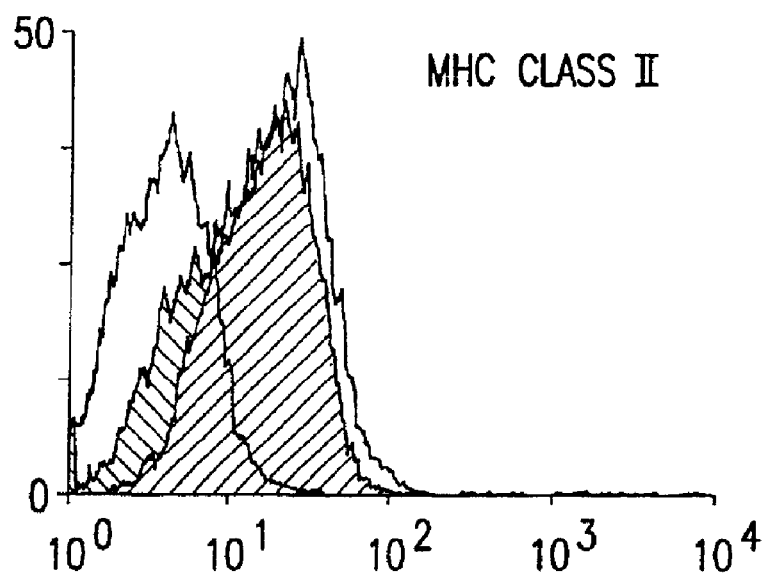
Figure 3F:
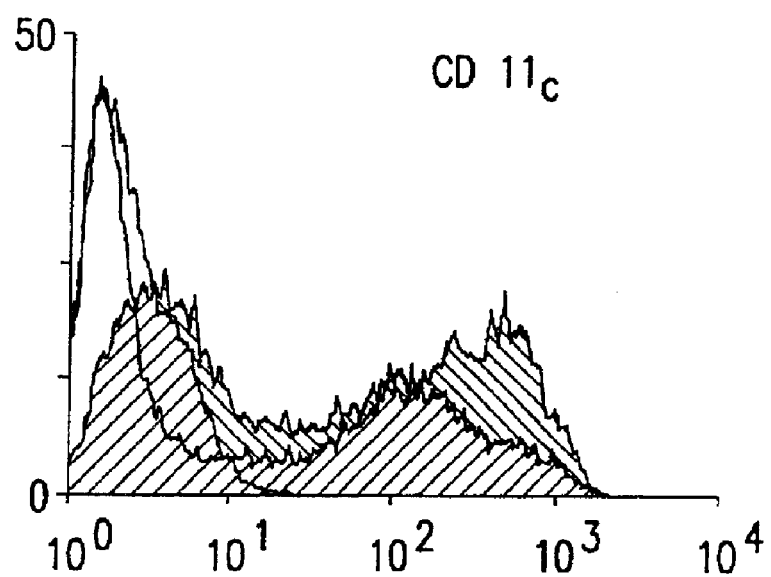
Figure 4A:
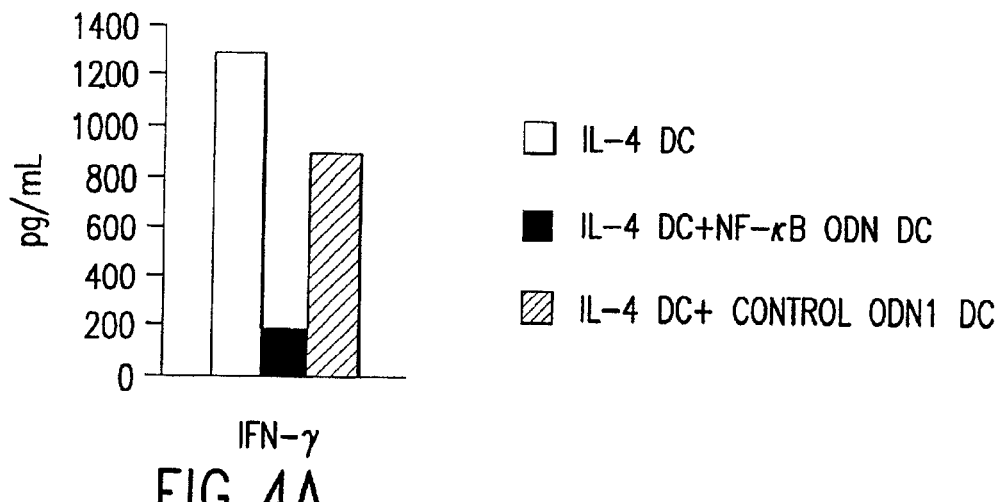
FIG. 4 is a bar graph showing the ability of NF-κB ODN DCs to differentially inhibit TH1 cytokine production in vitro. DCs isolated from B10 bone marrow and propagated with GM-CSF+IL4 (unfilled bars) in the presence of NF-κB ODN (black bars) or control ODN1 (striped bars).
Figure 4B:
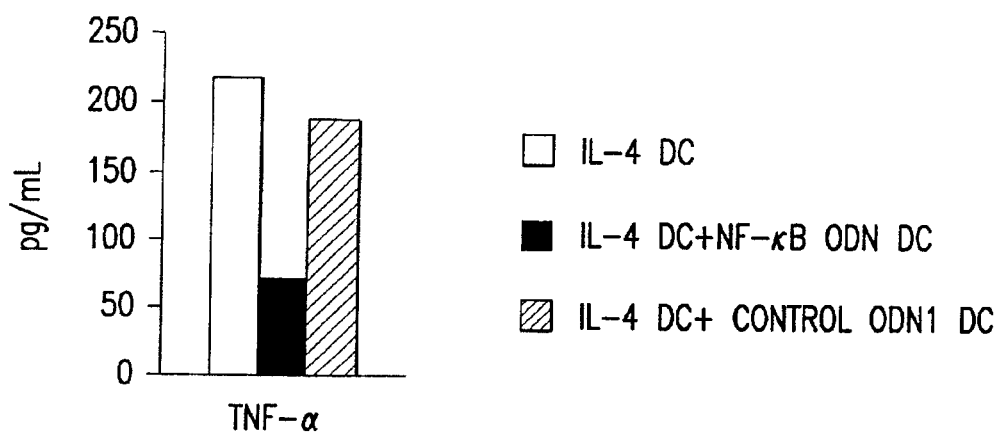
Figure 4C:
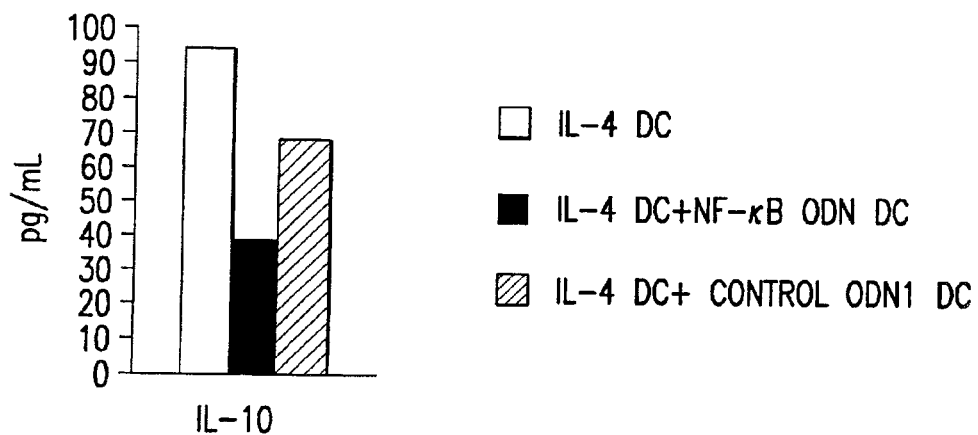
Figure 4D:
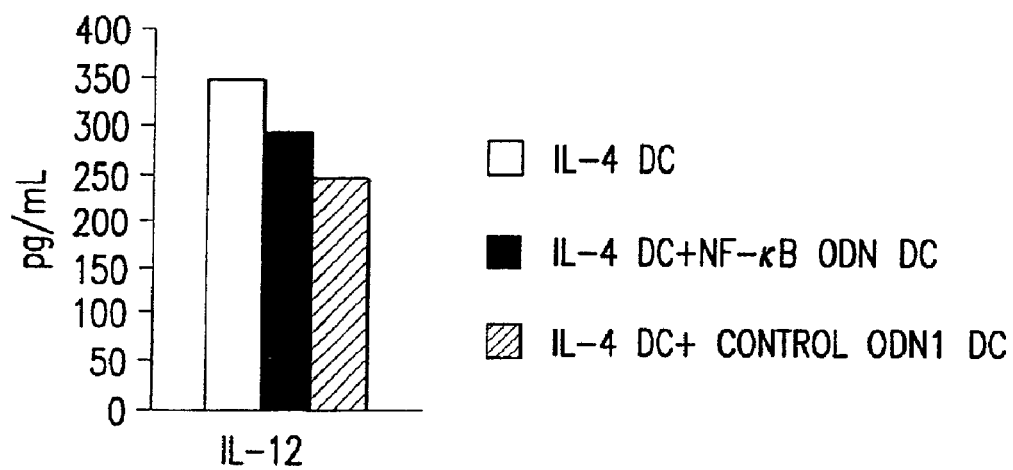
Figure 4E:
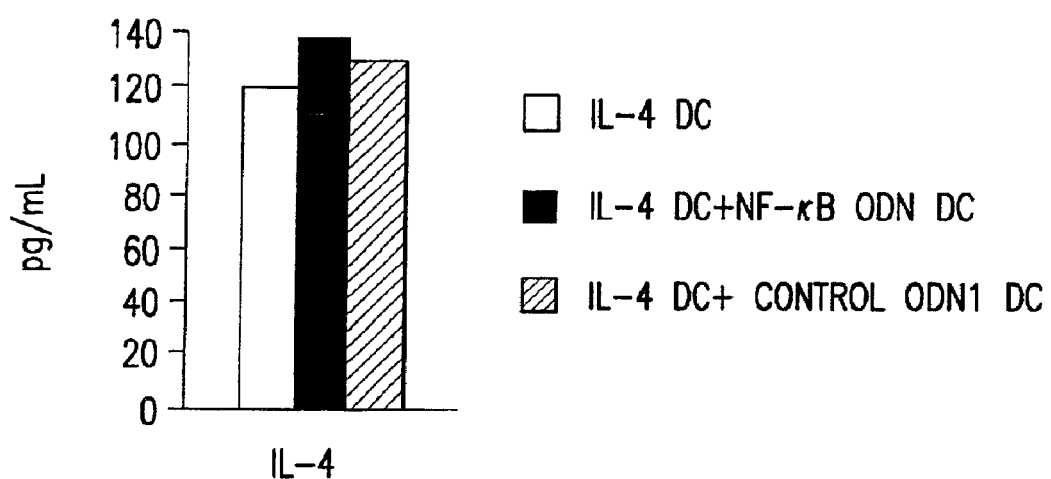

Bone marrow-derived DCs produce nitric oxide (NO), which is NF-κB transcription-dependent, in response to lipopolysaccharide (LPS) stimulation. See Lu et al., *J. Immunol.* 157:3577–3586 (1996). To determine whether NF-κB ODN decoys could prevent LPS-stimulated NO production by DCs, GM-CSF+IL-4 DCs exposed to NF-κB ODN or control ODN1 were treated with LPS for 18 hours. Supernatants were subsequently collected to quantitate nitrite levels as an index of NO production. NF-κB ODN-treated DCs released minimal amounts of nitrite in response to LPS, similar to levels observed in the culture media of control cells (FIG. 2). In contrast, LPS-stimulated DCs and DCs exposed to control ODN1 produced significantly larger amounts of NO.

Example 3

NF-κB ODN Effects on the Cell-Surface Expression of Co-Stimulatory Molecules A. Materials and Methods Expression of cell surface antigens on DCs was analyzed by cytoflourography, using an EPICS ELITE™ flow cytometer (Coulter Corporation, Hialeah, Fla.). Cells were stained with the primary hamster or rat monoclonal antibodies (mAbs) CD40, CD80 or CD86 (PharMingen, San Diego, Calif.) followed by fluorescein isothiocyanate (FITC)-conjugated goat anti-hamster or goat anti-rat IgG2a, as described previously by Lu et al., *Transplantation* 60:1539–1545 (1995), incorporated herein by reference. MHC class II was detected with biotin conjugated mAbs using FITC-streptavidin as the secondary reagent.

B. Results

Functional maturation of DCs is associated with upregulation of co-stimulatory signals (CD40, CD80 and CD86). DCs propagated in GM-CSF alone do not express high levels of these markers and are phenotypically and functional considered immature until exposed to IL-4 which commits them to full maturity. These mature DCs express high levels of class I and class II MHC as well as costimulatory molecules. See Fu et al., *Transplantation* 62:659–665 (1996) and Fu et al., *Transplant Proc.* 29:1310 (1997), incorporated herein by reference.

To determine the effect of NF-κB inhibition on cell surface phenotypic DC maturation, DCs were propagated from B10 (H2b) in GM-CSF+IL-4 in the presence or absence of NF-κB ODN from the start of culturing. After 5 days of culturing, the expression of these molecules on the surface of the DCs was analyzed using a panel of mAbs and detected by flow cytometry. As shown in FIG. 3, expression of MHC class II and the DC marker CD11c on the surface of NF-κB ODN-treated DCs was similar to that found on the surface of GM-CSF+IL-4-treated DCs. Furthermore, the same level of expression was seen in DCs propagated in GM-CSF+IL-4 and exposed to control ODN1. MHC class I and CD40 expression were slightly impaired by NF-κB ODN treatment. Significant inhibition of CD80 and CD86 expression was observed in NF-κB ODN-treated DCs compared to untreated DCs or control ODN1-treated DCs which expressed high levels of costimulatory molecules on their surface.

Thus competitive inhibition of NF-κB by NF-κB ODN prevents maturation of DCs, regardless of the presence of the promaturation IL-4 signal. This is in contrast the inhibition of NF-κB-mediated maturation by the calcineurin inhibitor, cyclosporine A (CsA). See Lee et al., *Transplantation* 68:1255–1263 (1999). These results indicate that NF-κB ODN-treated DCs will likely not readily mature when administered to a host and exposed to a proinflammatory microenvironment, whereas other propagated immature DCs are likely to mature when exposed to a proinflammatory microenvironment.

Example 4

Effect of NF-κB ODN-treated DCs on T-cell Cytokine Production

A. Materials and Methods

All DCs were cultured with allogeneic C3H spleenic T cells at a T cell/DC ratio of 10:1 for 4 days. Cytokines were detected in the supernatant by ELISA.

B. Results

The nature of T-cell responses stimulated by NF-κB ODN-treated DCs was examined since the phenotype of NF-κB ODN-treated DCs, as indicated in Example 3, strongly suggested tolerogenic potential. To determine whether NF-κB ODN-treated DCs could effect the nature of T-cell responses, the cytokine release pattern of DC T-cell co-cultures was evaluated. Supernatants were collected from 4 day co-cultures consisting of T-cells and irradiated DCs from completely allogeneic mice at a T-cell:DC ratio of 10:1. Cytokine release was detected by ELISA. Mature DCs elicited IFN-γ, TNF-α, and IL-10 production by T-cells (FIG. 4). In contrast, co-stimulatory molecule-deficient NF-κB ODN-treated DCs did not induce these cytokines in allogeneic T-cells. Production of these inflammatory cytokines by T-cells was dramatically inhibited when stimulated by NF-κB ODN-treated DCs, whereas control ODN1-treated DCs had no such effect. Levels of IL-2, IL-4 and TGF-β were not affected by NF-κB ODN DCs.

Example 5

DC Allostimulatory Capacity is Inhibited by NF-κB ODN

A. Materials and Methods

One way mixed leukocyte reactions (MLR) were performed in 96 well, round bottom microculture plates (Coming Glassworks, Corning, N.Y.). Graded doses of γ-irradiated (20 Gy) syngeneic (C3H) or allogeneic (B10) stimulator cells were added to $2 \times 10^5$ nylon wool-eluted C3H spleen cells (responders), and maintained in culture for 72 hours. $^3$H-thymidine (1 mCi/well) was added for the last 18 hours of culture. Cells were harvested onto glass fiber mats using an automatic system, and $^3$H-thymidine incorporation was determined by liquid scintillation counter.

B. Results

Figure 5:
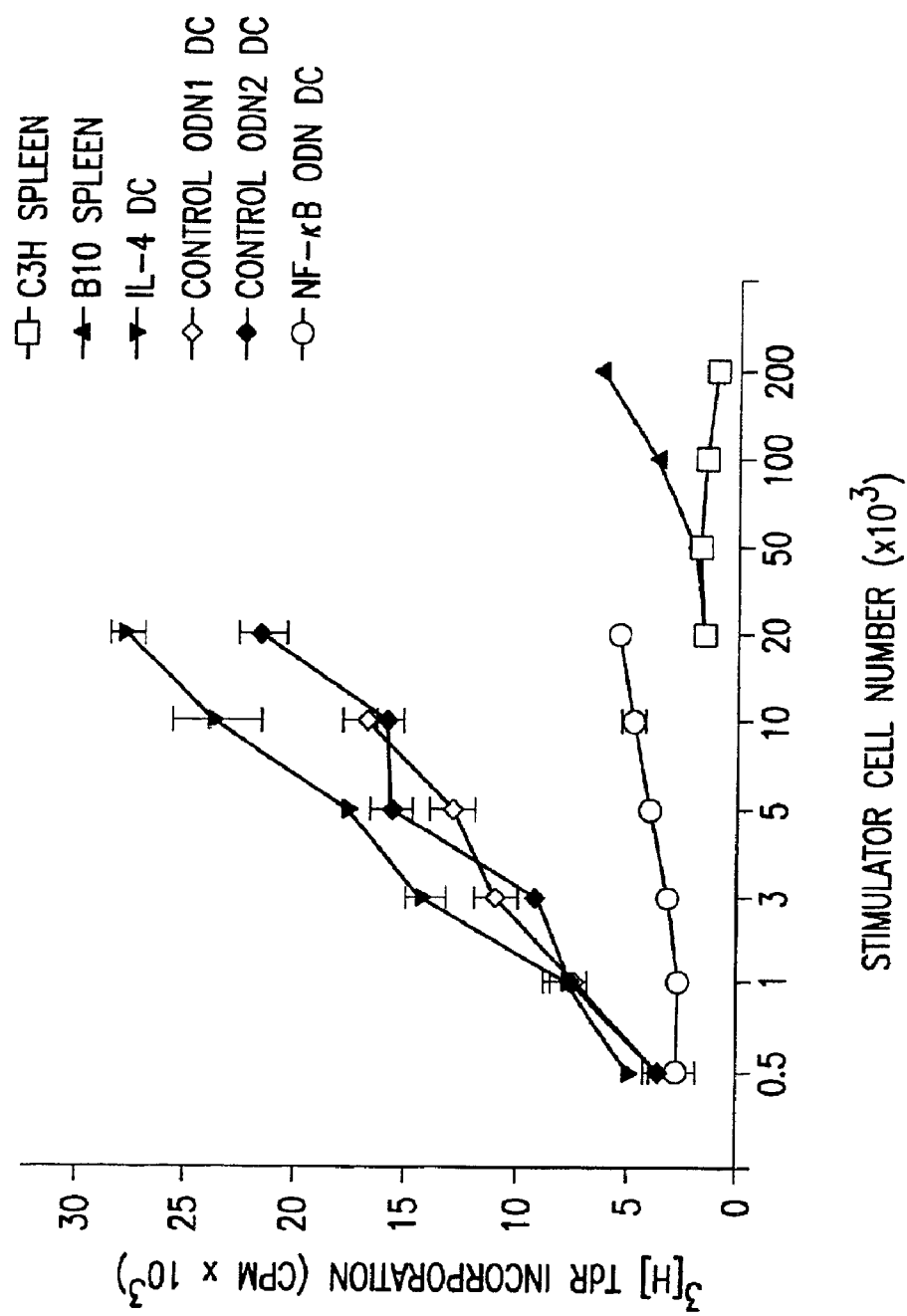
FIG. 5 is a graph showing the inhibition of allostimulatory function of DCs exposed to NF-κB ODN. The results are expressed as counts per minute (CPM) (mean±SD).
Figure 6:
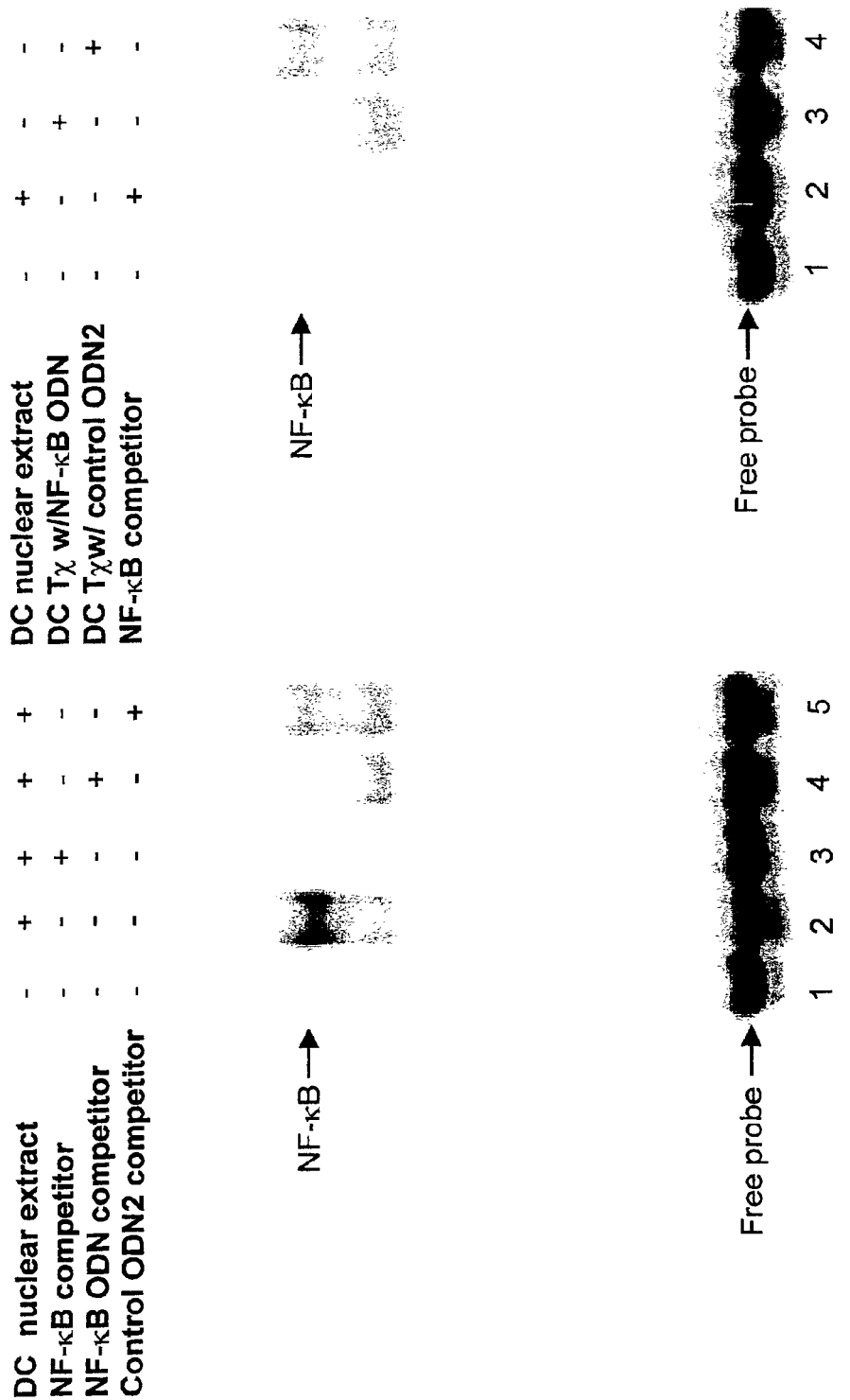
FIG. 6 is an autoradiogram showing the specific binding of NF-κB ODN to NF-κB protein and the inhibition of NF-κB DNA binding activity by NF-κB ODN. (A) Shows the ability of NF-κB to specifically bind NF-κB protein. Lane 1 shows free probe in the absence of nuclear proteins. Nuclear proteins are present in lanes 2–5. Lane 2 demonstrates that the presence of NF-κB in nuclear extracts incubated with radiolabelled NF-κB probe. Excess unlabeled probe was added as competitor for the radiolabelled probe in the binding reaction shown in lane 3. Excess unlabeled NF-κB ODN decoy was added as competitor for the radiolabelled probe in lane 4 and competition with excess unlabeled control ODN2 is shown in lane 5. (B) Shows the inhibition of NF-κB DNA-binding activity in DCs treated with NF-κB ODN. DCs were propagated with GM-CSF+IL4 in the presence of NF-κB ODN or control ODN2. EMSA was performed using the identical radiolabelled probe indicated in A. Lane 1 shows free labeled probe in the absence of nuclear proteins. Lane 2 shows the results of the binding reaction that included untreated DC nuclear lysate, excess unlabeled NF-κB probe and labeled NF-κB probe. Lane 3 shows the band observed following the binding reaction in which lysates obtained from DCs exposed to NF-κB decoys in culture were incubated with labeled NF-κB probe. Nuclear extract lysates from DCs treated in culture with control ODN2 and then incubated with the radiolabelled NF-κB-specific probe are shown in lane 4.

The effect of NF-κB ODN on DC immunostimulatory activity, as evaluated by in vitro MLR since NF-κB ODN-treated DCs selectively altered the cytokine production of allogeneic T-cells to a profile suggesting immunosuppressive potential. Allogeneic T-cells from the spleen of C3H mice (H2K) were stimulated by DC propagation from B10 bone marrow progenitors (H2b) and exposed to NF-κB ODN or control ODN1. In initial experiments, a significantly impaired allostimulatory capacity of NF-κB ODN-treated DCs was observed. However, exposure to control ODN1 that consists of an entirely random sequence, conferred a degree of impaired alloreactivity to the DCs, albeit not as significant as NF-κB ODN-treated DCs. Therefore, another control ODN, containing a partial NF-κB consensus sequence (ODN2) was designed. The GGGG quartet was not included in ODN2 or ODN1 (although ODN1 contains two GGG triplets) since it may behave in a sequence-nonspecific aptameric manner. As shown in FIG. 5, NF-κB ODN treatment of DCs markedly impaired their allostimulatory capacity in MLR when compared to DCs propagated n GM-CSF+IL-4 alone. Control ODN1 and control ODN2 both minimally suppressed DC allostimulatory capacity but not to the extent seen with NF-κB ODN (FIG. 5).

Example 6

NF-κB ODN Decoys Specifically Inhibit DNA Binding of NF-κB in DCs

A. Materials and Methods

Electrophoretic mobility shift assays (EMSAs) were performed using a commercially available kit (Promega, Madison, Wis.). Nuclear proteins were isolated (Andrews and Faller, *Nucleic Acids Res.* 19:2499 (1991), incorporated herein by reference) from $5 \times 10^5$ to $1 \times 10^7$ cultured DCs either in the presence of absence of NF-κB ODN decoy or control ODN2. Supplied with the commercial EMSA kit was an NF-κB oligonucleotide which was used as a probe:
Sense sequence of Promega supplied NF-κB oligonucleotide:

5' AGTTGAGGGGACTTTCCCAGGC 3' (SEQ ID NO: 7).

The probe was end-labeled with [γ-$^{33}$P] ATP (New England Nuclear, Boston, Mass.). Nuclear proteins were incubated with labeled probe and the mobility shift was detected by running the mixture on a 4% acrylamide gel. Shifted bands were visualized by autoradiography. Unlabeled ODNs were used as competitive inhibitors where indicated.

B. Results

To confirm that the NF-κB ODN decoys could specifically bind NF-κB, EMSA was performed with nuclear extracts obtained from GM-CSF+IL-4 DCs. Specificity of the NF-κB ODN for NF-κB binding was demonstrated by utilizing unlabeled NF-κB ODN as a competitor to a consensus NF-κB probe supplied by Promega. As shown in FIG. 6A, NF-κB protein was detected in nuclear extracts of DCs propagated in GM-CSF+IL-4 by its ability to bind to NF-κB probe and cause a shift in mobility of the probe (FIG. 6A, lane 2). Addition of excess unlabeled consensus NF-κB probe to the binding reaction resulted in the disappearance of the NF-κB band (lane 3). Similarly, addition of excess unlabeled NF-κB ODN to the binding reaction competed for the binding of NF-κB to the labeled NF-κB probe (lane 4). In contrast, no competition was observed when the binding reaction was performed in the presence of unlabeled control ODN2 (lane 5).

To assess whether exogenously added NF-κB ODN decoys could interfere with DNA binding of NF-κB in DCs, DCs were propagated from bone marrow progenitors with GM-CSF+IL-4 in the presence or absence of NF-κB ODN decoys or control ODN2. After a 5 day culture, nuclear NF-κB binding activity was determined by EMSA. As shown in FIG. 6B, NF-κB binding activity was detected in nuclear extracts of GM-CSF+IL-4 DCs. The addition of NF-κB ODN to these cultured cells completely inhibited binding (lane 3) whereas addition of control ODN2 had no effect (lane 4). These data demonstrate that addition of NF-κB ODN to DCs is able to block NF-κB DNA binding activity.

Example 7

NF-κB ODN Decoys Interfere with NF-κB-Dependent Transcription in DCs

A. Materials and Methods

NF-κB ODN-treated and control ODN2-treated DCs were transfected with a reporter construct containing the luciferase gene fused to a sequence of 5 consensus NF-κB binding sites separated by short spacer sequences (Stratagene, La Jolla, Calif.). Transfections were performed with 1 μg of plasmid per treatment group ($1 \times 10^5$ cells) and LipofectAmine™ (GibcoBRL, Gaithersberg, Md.) in serum-free RPMI 1640 for 5 hours. Fresh medium was then added and the cells were further cultured with 10 μg/ml LPS for 18 hours. Cells were subsequently washed and lysed. Luciferase activity was determined using a commercially available kit (Promega, Madison, Wis.).

B. Results To Assess Whether Diminished DNA Biding of Nuclear NF-κB in DCs by

Figure 7:
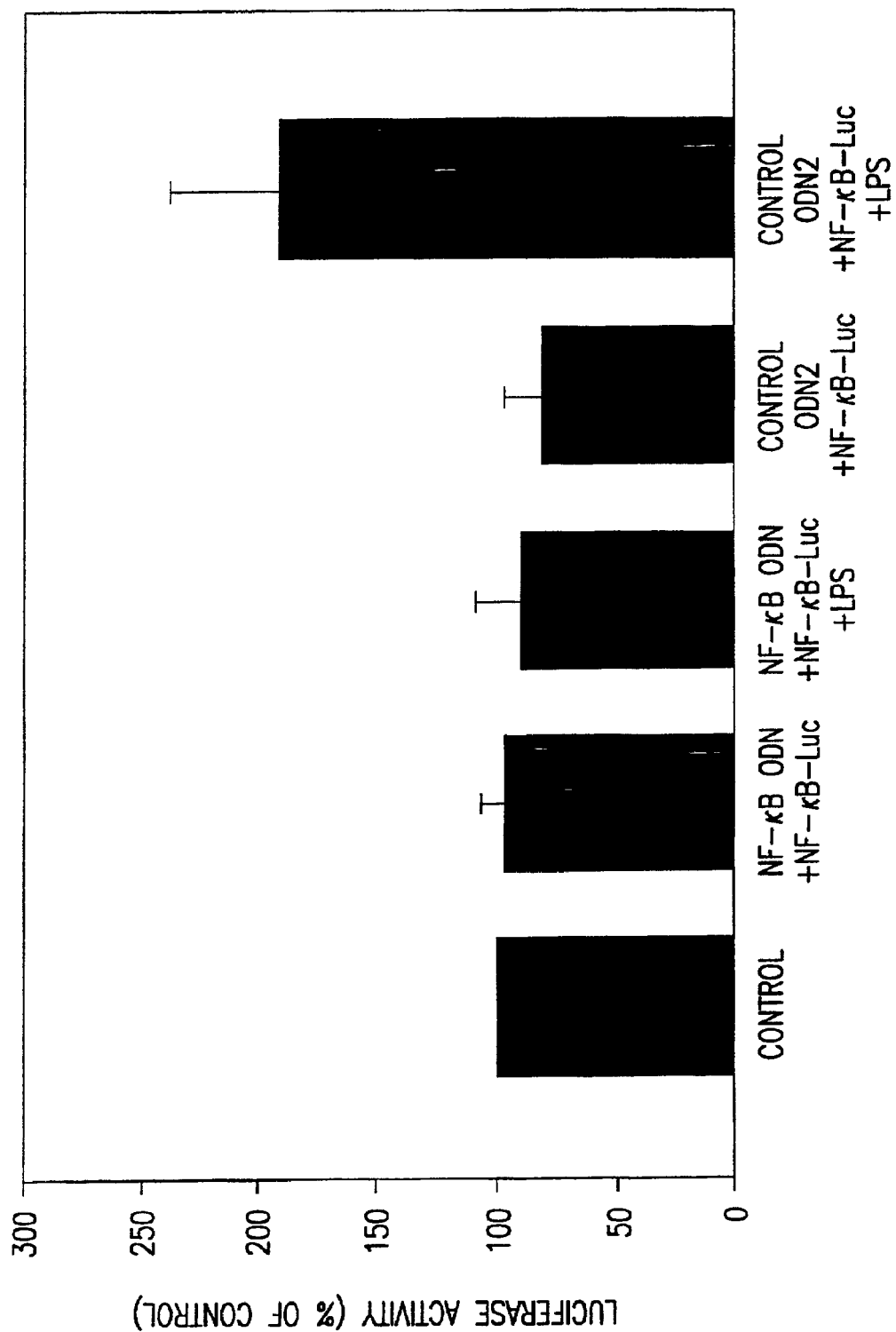
FIG. 7 is a bar graph showing the ability of NF-κB ODN to inhibit NF-κB-dependent gene transcription in DCs. Non-transfected cells served as control.

NF-κB ODN was associated with inhibition of NF-κB-dependent transcription, transient transfection of DCs cultured with GM-CSF+IL-4 in the presence of NF-κB ODN or control ODN2 was performed using a luciferase reporter gene fused to NF-κB biding sites and subsequently stimulated by 10 μg/ml LPS for 18 hours. As shown in FIG. 7, upon LPS stimulation, luciferase activity significantly increased in DCs propagated in GM-CSF+IL4 as well as in control ODN2-treated GM-CSF+IL4 DCs. In contrast, DCs exposed to NF-κB ODN before and during LPS stimulation prevented expression of luciferase activity in DCs, with levels no different than nontransfected controls.

Example 8

NF-κB ODN-treated DCs Can Prolong Foreign Graft Survival

A. Materials and Methods

Heterotropic heart transplants: Fully allogeneic intra-abdominal vascularized heart transplantation was performed from normal B10 donors to size matched C3H recipients as previously described. See Fu et al., *Transplantation* 62:659–665 (1996). Allograft survival was assessed by daily trans-abdominal palpitation of the heart. Cessation of heartbeat indicated rejection of the allograft and was subsequently confirmed histologically. To assess the effect of DCs on allograft survival, animals received one injection of $2 \times 10^6$ cells administered intravenously through the lateral vein 7 days prior to the heart transplantation in the absence of immunosuppression. Control groups received either no treatment (PBS), freshly-isolated bone marrow cells, or DC propagated with GM-CSF+control ODN2.

Statistical Analysis: Differences in mean allograft survival were detected using the Kruskal-Wallis test. Pairwise comparisons were performed using the Wilcoxon rank sum test. P values<0.05 were considered insignificant.

B. Results

Figure 8:
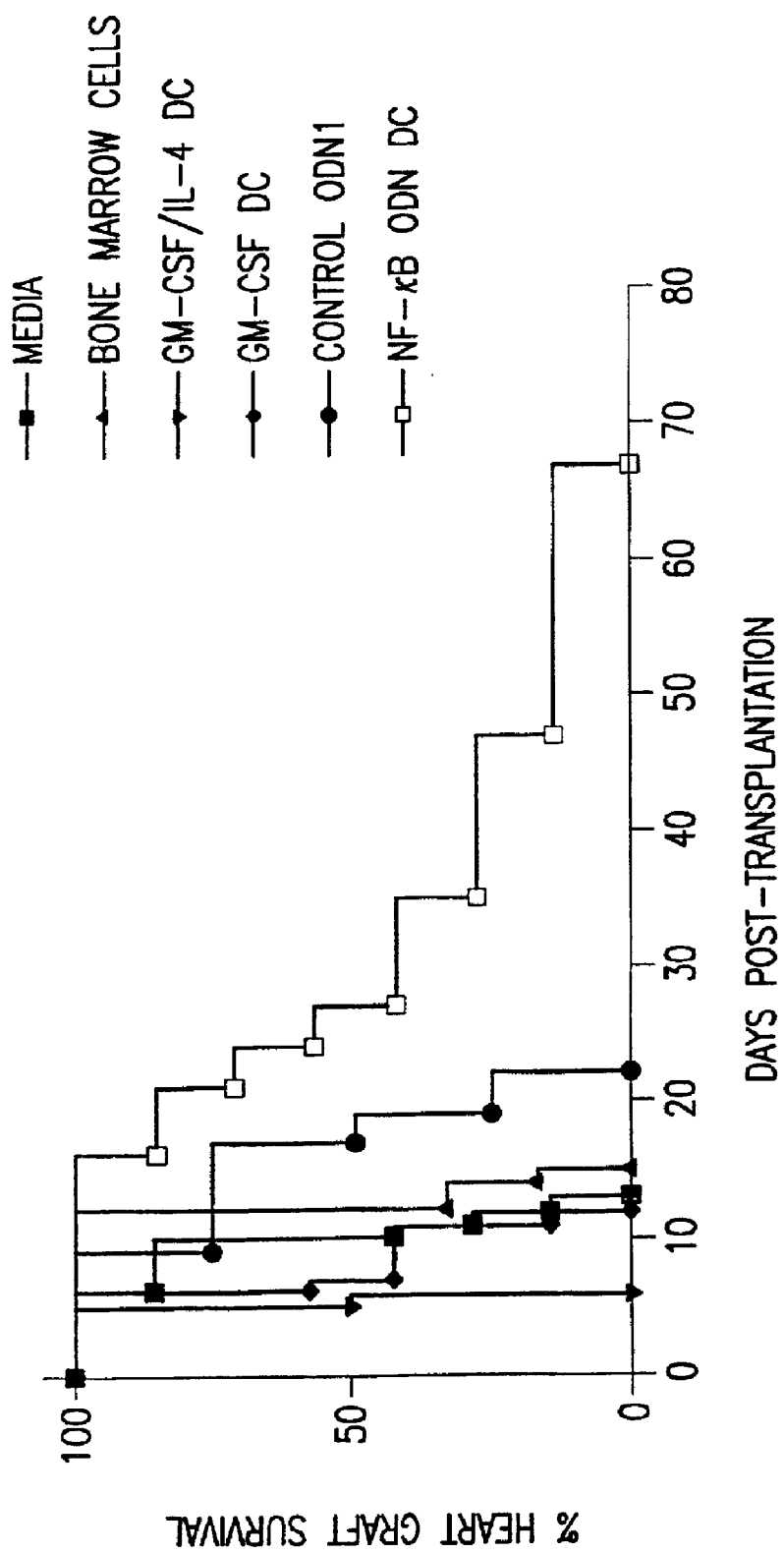
FIG. 8 is a graph showing actuarial survival curves of B10 heart allografts in C3H recipient injected with NF-κB ODN-treated donor DCs.

As shown in FIG. 8 and Table 1 below, donor mature DC (IL-4 DC) pretreatment accelerated heart allograft rejection.

In FIG. 8, the mean survival time (MST) was 5 days in treated animals, versus 10 days in untreated animals, p<0.01; 11 days in GM-CSF DCs group, p<0.01. Infusion of donor NF-κB ODN DCs prior to transplantation significantly prolonged heart allograft survival (MST 27 days, p<0.001 versus IL-4 DC); see FIG. 8. Control ODN1 DC infusion also led to a slight increase in heart allograft survival (MST 18 days, p<0.22 versus GM-CSF DC), but not to the level achieved with NF-κB ODN DCs treatment (p<0.005); see FIG. 8. Table 1 shows that pretreatment with NF-κB ODN DCs transfected with adenovirus encoding CTLA4Ig (fusion protein containing CTLA4 and mouse Ig) further significantly prolonged heart allograft survival (MST 70 days).

TABLE 1

| PRETREATMENT | Hear Allograft Survival (MST) |
| --- | --- |
| PBS | 10 |
| GM-CSF DC | 14 |
| GM-CSF + TGFβ DC | 26 |
| GM-CSF + NFκB-ODN DC | 32 |
| GM-CSF + Ad-CTLA4Ig + NFκB-ODN DC | 70 |
| GM-CSF + Ad-eGFP + NFκB-ODN DC | 29 |
| GM-CSF + Ad-CTLA4Ig DC | 12 |
| GM-CSF + Ad-eGFP DC | 9 |

Example 9

NF-κB ODN-treated DCs Maintain Tolerogenicity When Infected with a Viral Vector

Figure 9A:
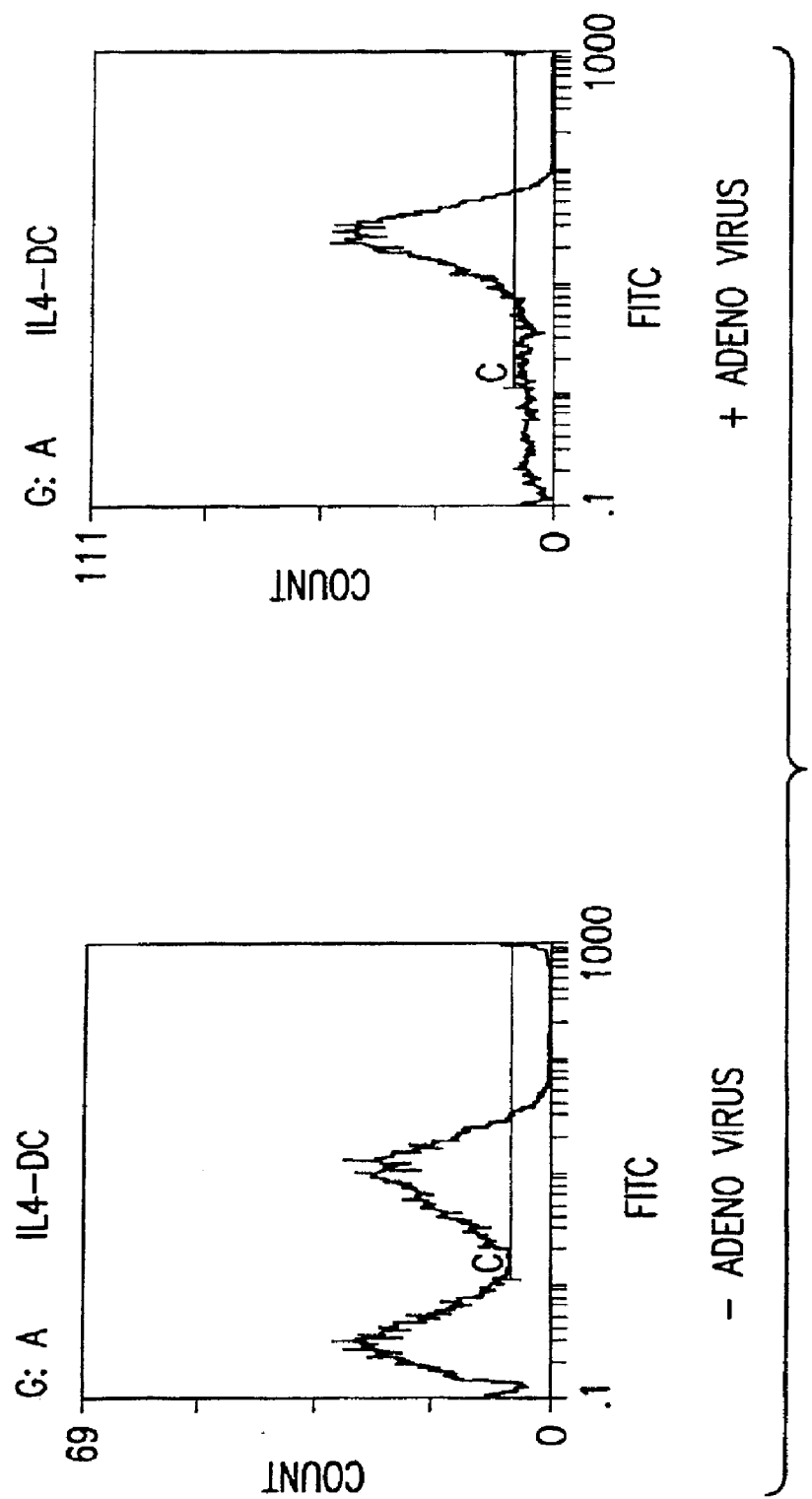
FIG. 9 shows flow cytometric analysis showing the inhibition of costimulatory molecule (B7-2) expression in NF-κB ODN DCs in the presence and absence of an adenoviral vector. (A) Adenoviral vector up-regulates B7-2 expression in IL-4-treated DCs. (B) Adenoviral vector up-regulates B7-2 expression in TGF-β-treated DCs. (C) Adenoviral up-regulation of B7-2 expression in DCs is prevented in DCs treated with NF-κB ODN.
Figure 9B:
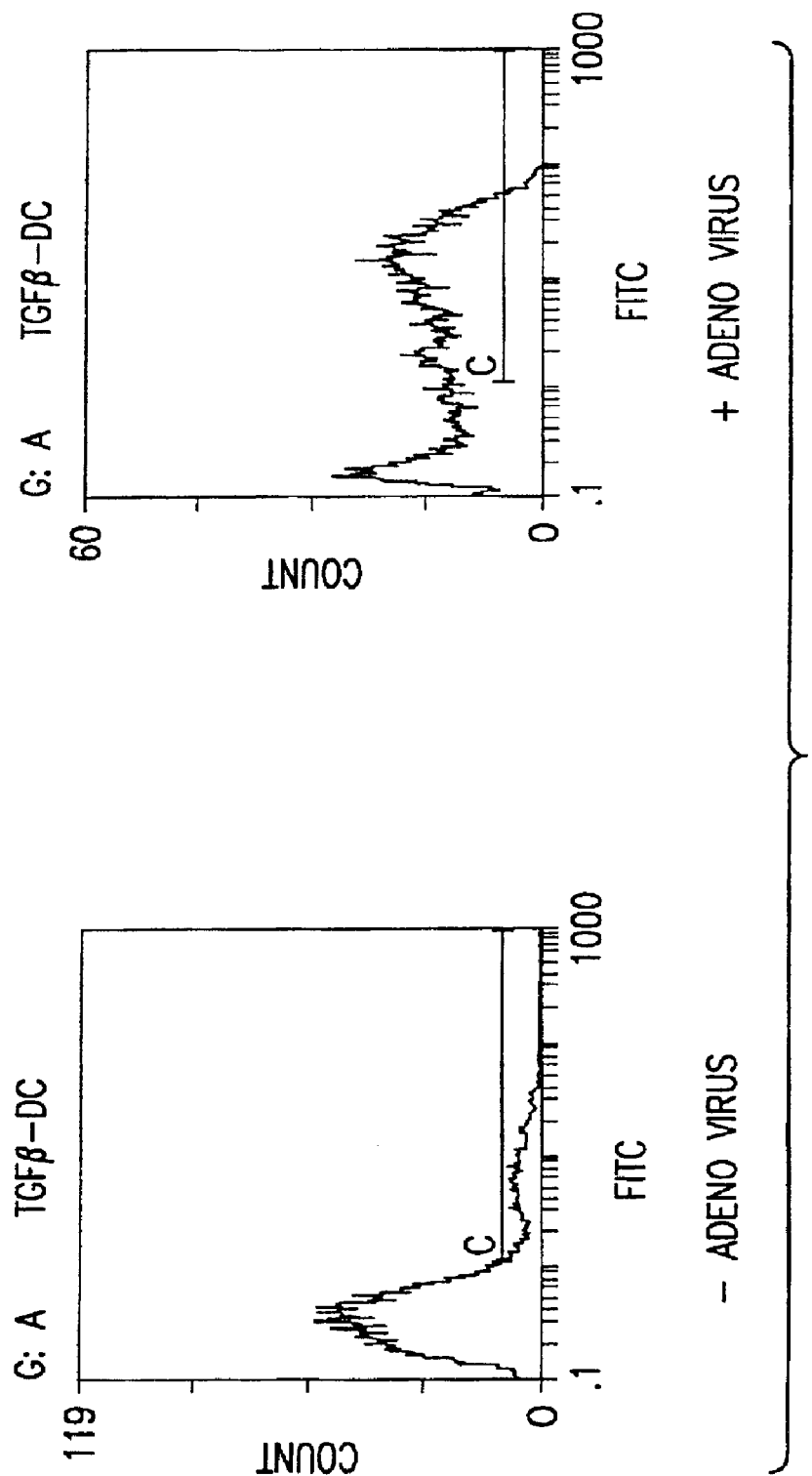
Figure 9C:
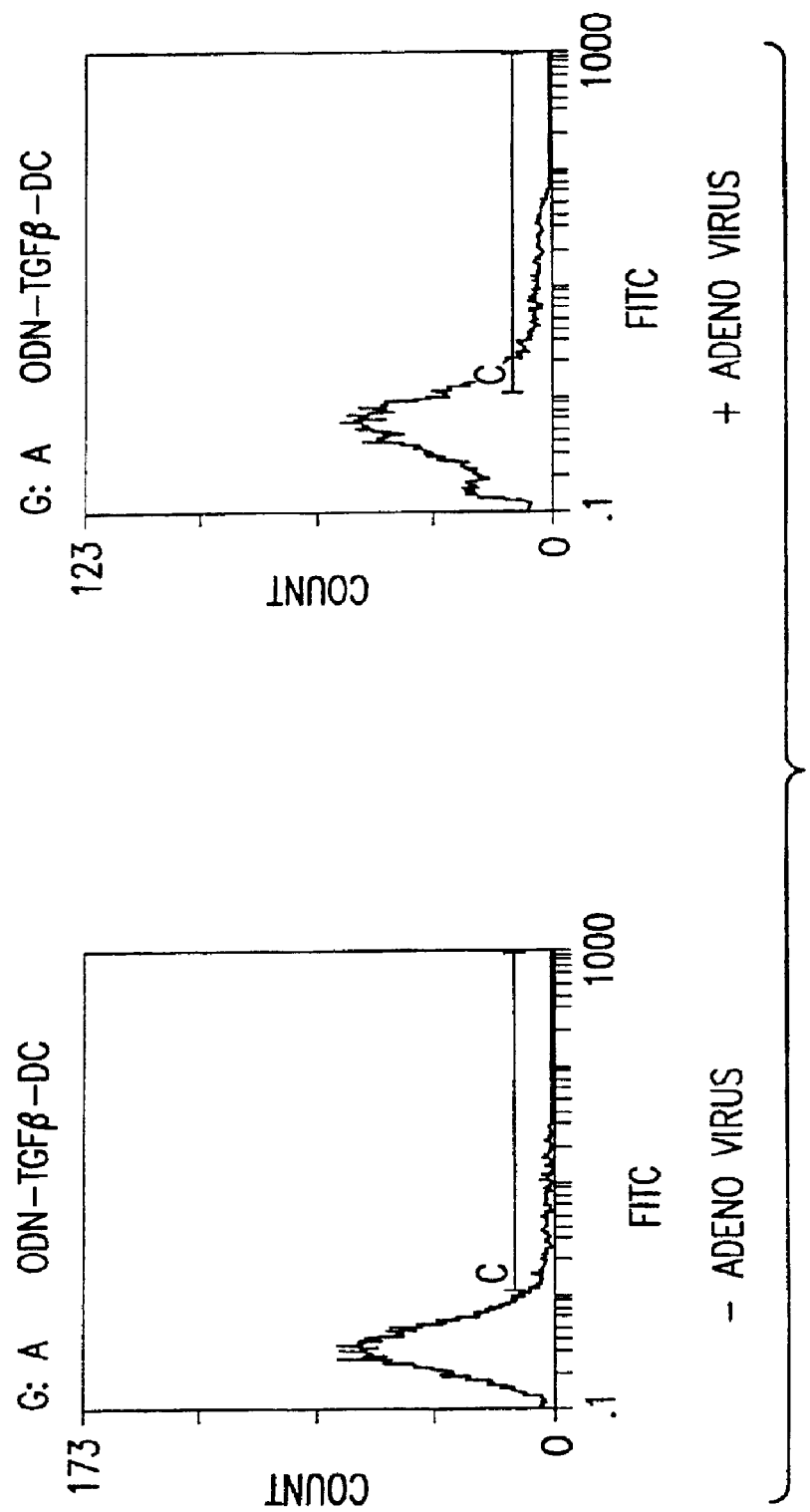
Figure 12:
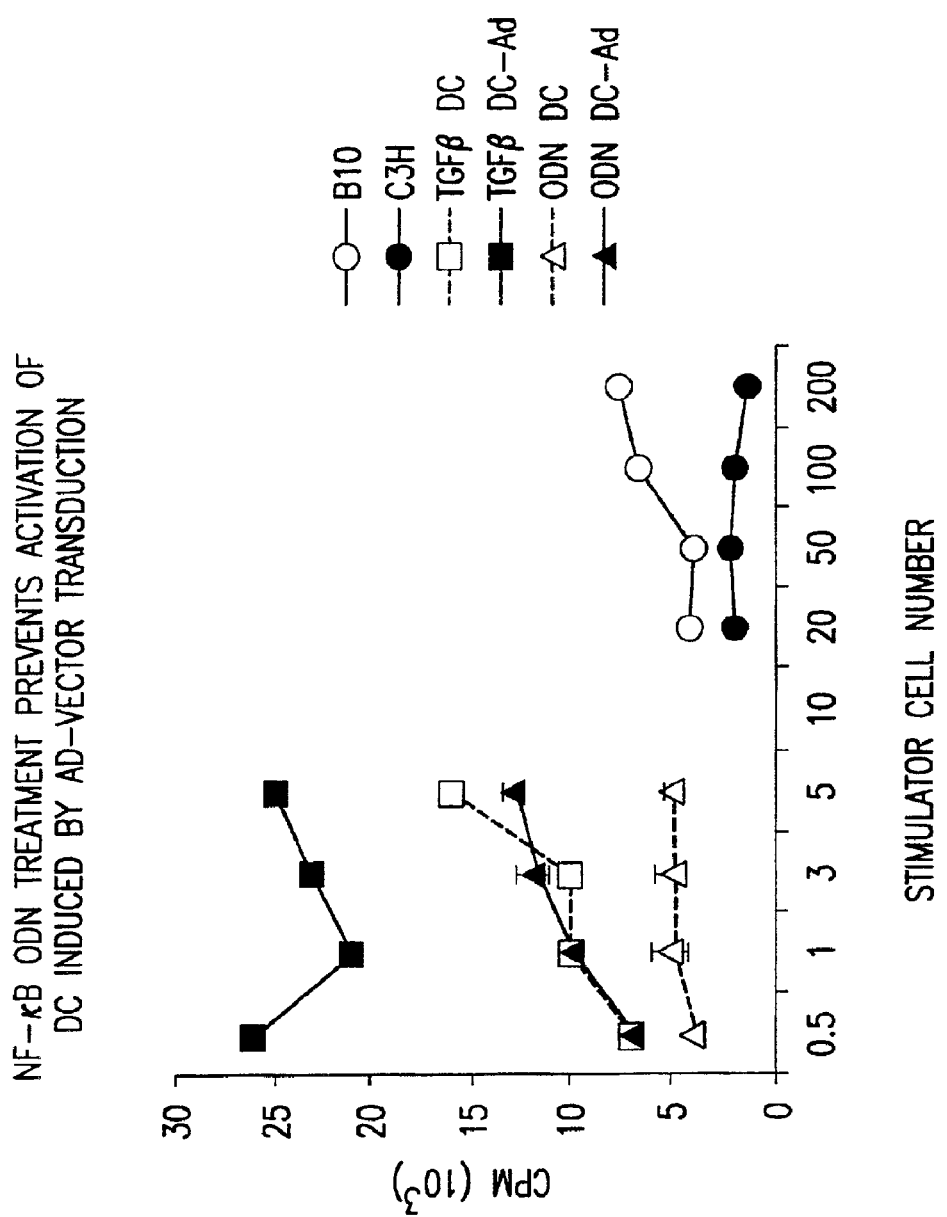
FIG. 12 is a graph showing the ability of NF-κB ODN to block adenoviral induced DC activation.

As noted above, adenoviral vector expression in DCs results in the activation of DCs and the up-regulation of costimulatory molecules on the surface of DCs. See Lu et al., *J. Leukocyte Biology Supplement* 2, Abstract B52 (1998). FIG. 9A shows that NF-κB ODN prevented the up-regulation of costimulatory molecule expression (B7-2) on mature DCs (IL4-DC) by adenoviral vector infection. FIG. 9B (TGF-β-DC) and 9C (GM-CSF-DC) show the effects of costimulatory molecule expression on immature DCs after infection with an adenoviral vector in the presence of NF-κB ODN. FIG. 11 also shows that NF-κB ODN prevented the up-regulation of costimulatory molecule expression (CD86) by adenoviral vector infection. In contrast, neither IL-4 DCs or TGF-β DCs were able to prevent the upregulation of costimulatory molecule expression (CD86; FIG. 11). The results indicated that NF-κB ODN prevents the up-regulation of costimulatory molecules on DCs by adenoviral vector infection. FIG. 12 shows that NF-κB ODN prevents the activation of DCs induced by adenovirus transfection (as measured by the allostimulatory capacity of the DCs described above in Example 5).

Figure 10:
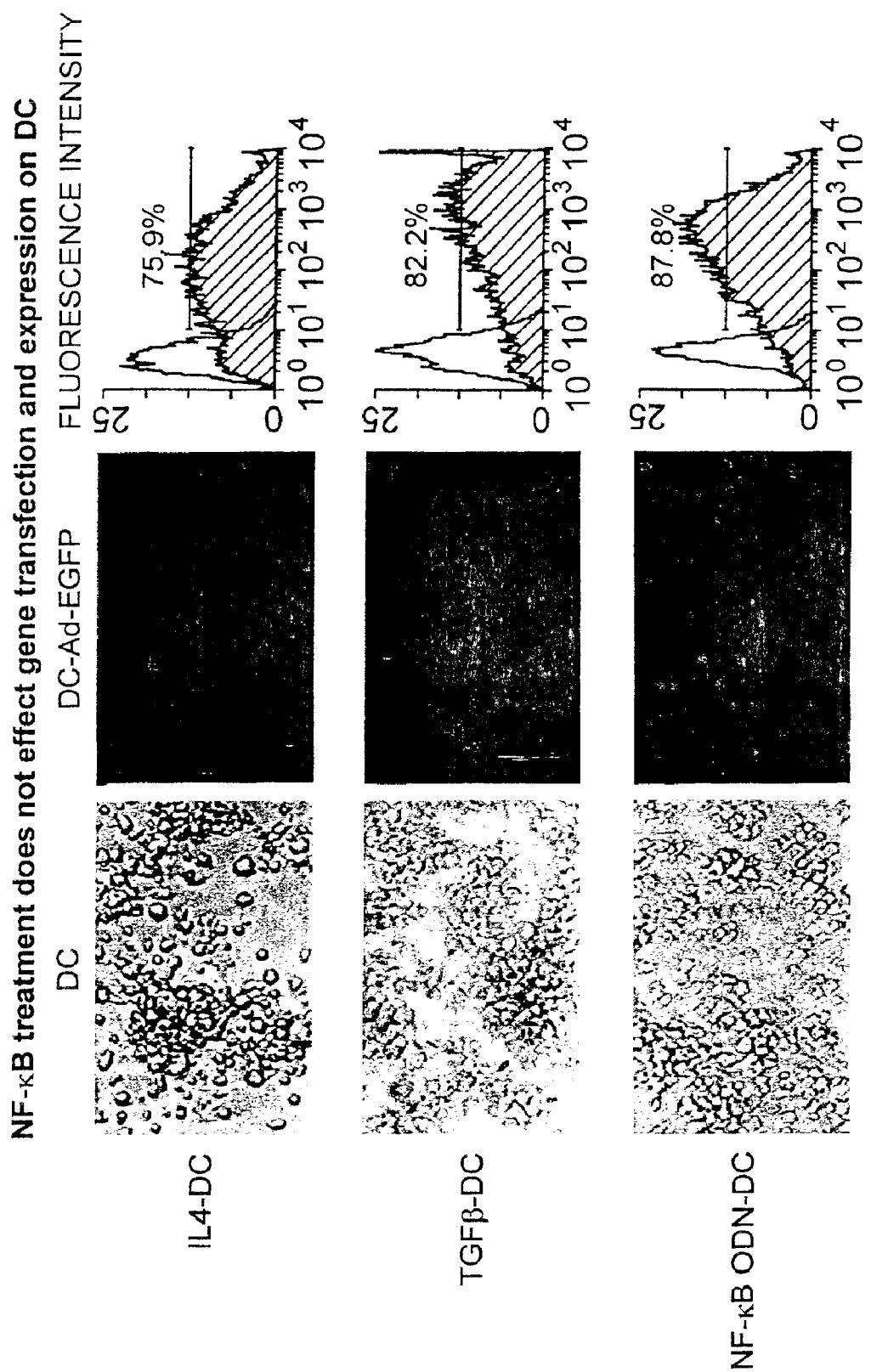
FIG. 10 shows the efficient adenoviral vector infection of DCs. (A) fluorescence microscopy of DCs treated with IL-4 infected with adenoviral vector expressing green flourescent protein (Ad-EGFP). (B) fluorescence microscopy of DCs treated with TGF-β infected with Ad-EGFP. (C) fluorescence microscopy of DCs treated with NF-κB ODN infected with Ad-EGFP. The graphs on the right hand side of the figure are flow cytometry analyses showing the % of Ad-eGFP infected cells.

In addition, NF-κB ODN treatment of DCs did not interfere with the efficiency of infection with an adenoviral vector containing the transgene e-GFP (green fluorescence protein) which was used as a reporter gene. FIG. 10 shows that mature (IL-4-DC; FIG. 10A) and immature DCs (GM-CSF+TGF-β-DC, FIG. 10B; and GM-CSF-DC+TGF-β-DC+NF-κB ODN; FIG. 10C) were efficiently infected by Ad-eGFP. The cells were infected with a multiplicity of infection (MOI) of 5. The left-most panel shows the cells, the middle panel shows the expression of eGFP in the cells, and the right-most panel shows a graph of flow cytometry analyses showing the % of Ad-eGFP infected cells. The data indicate that the presence of NF-κB ODN did not interfere with adenoviral infection or expression of eGFP. In fact, there was an increase in the number of cells expressing eGFP in the cells treated with NF-κB ODN.

Figure 14:
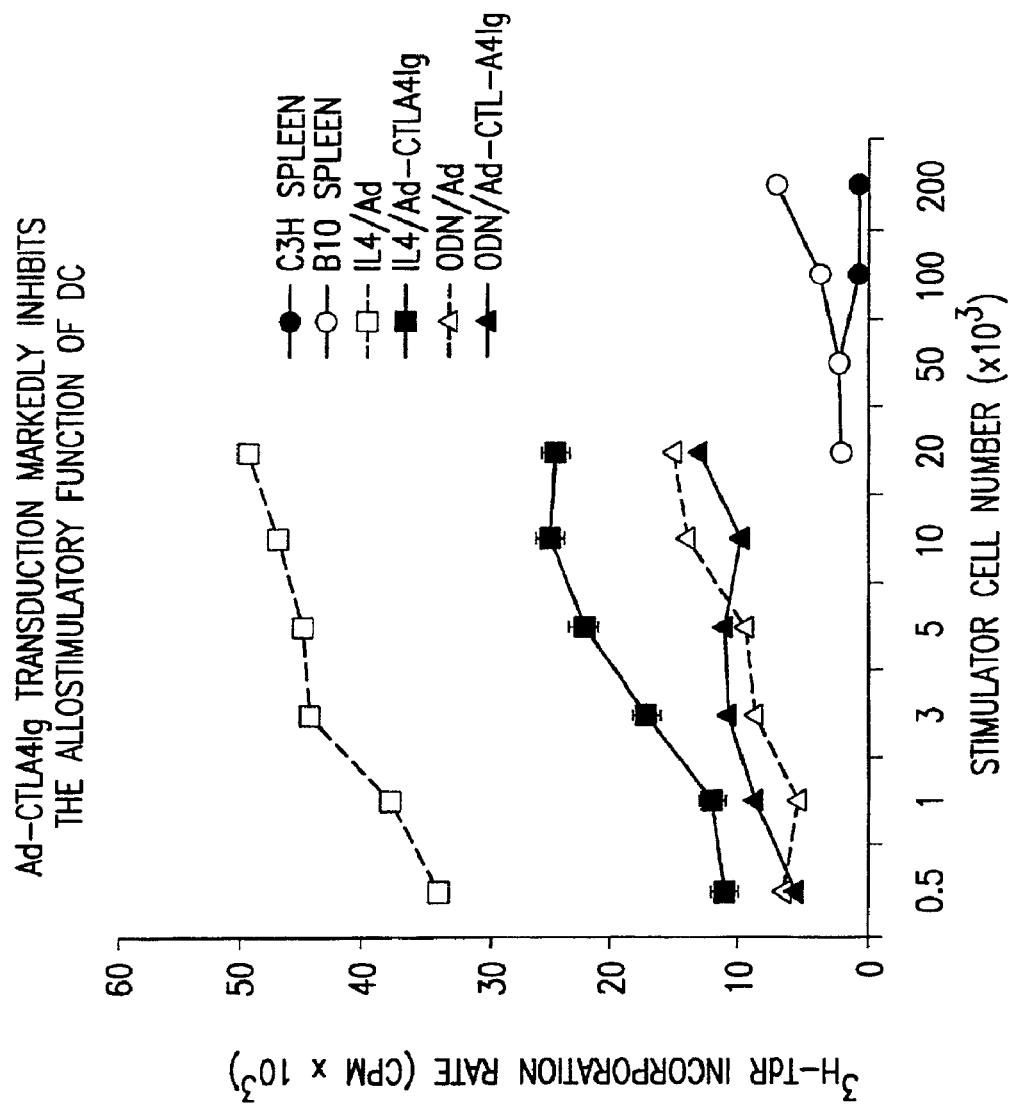
FIG. 14 is a graph showing that adenoviral CTLA4 Ig transgene expression inhibits the allostimulatory function of DC and that this effect is further enhanced by the presence of NF-κB ODN.

Furthermore, NF-κB ODN treatment of DCs did not interfere with the efficiency of infection with an adenoviral vector encoding CTLA4Ig (CTLA4Ig is a fusion protein containing CTLA4 and mouse Ig). CTLA-4 gene expression was detected using the indicator cell line (M38 B7-1$^+$; control cells were M38 B7-1$^-$). See FIG. 13. The supernatant from either TGF-β DCs transfected with an adenovirus encoding CTLA4IG or NF-κB ODN transfected with an adenovirus encoding CTLA4IG was collected and coincubated with the control cells or indicator cells for ½ hour at 4° C. The supernatant was then washed and the cells were incubated with a 2° anti-mouse antibody (which can bind to the mouse Ig of CTLA4Ig fusion protein). The 2° antibody was washed from the cells and the cells were collected for flow cytometry analysis. FIG. 13 shows that CTLA4Ig was efficiently expressed in both TGF-p DCs and NF-κB ODN DCs. Moreover, DCs transfected with adenovirus expressing CTLA4Ig were capable of inhibiting the allostimulatory function of the DCs (see FIG. 14). The allostimulatory capacity of DCs transfected with adenovirus was determined according to the procedure described in Example 5 above. FIG. 14 shows that NF-κB ODN inhibited the allostimulatory capacity DCs both in the presence and absence of CTLA4Ig.

Example 10

Prevention of Type 1 Diabetes Development with NF-κB ODN

A. Materials and Methods

To determine whether NF-κB ODN DCs were capable of inhibiting type 1 diabetes development, non-obese diabetic (NOD) mice were used, which is an art recognized model for diabetes development. See Todd, J. A., 1997, *Pathol. Biol.* 45:219–227 and Salomon et al., 2000, *Immunity* 12:431–440. At age 7 weeks, female NOD mice were treated with DCs. The DCs were isolated from NOD mice in accordance with the methods described in Example 1 above. The DCs were then propagated in the presence of either NF-κB ODN or IL-4 for 5 days and then pulsed with islet antigen (AG) where indicated. The mice were injected with $2 \times 10^6$ DCs and diabetes development was monitored by electronic glucometer. A glucose serum level of>350 mg/ml was indicative of diabetes development.

Intact islets from NOD mice (between 4–5 weeks old) were isolated by controlled collagenase digestion of perfused pancreas. The islets were handpicked to ensure purity from any non-endocrine tissue. The islets were then collected in phosphate-buffered saline subjected to five cycles of freeze-thawing (37° C. for 5 minutes, −80° C. for 5 minutes). The lysate was then adjusted with PBS to provide 1 islet cell per 10 DC. DC were then pulsed overnight with the appropriate volume of islet lysate, washed extensively and injected into the NOD mice.

B. Results

Figure 16:
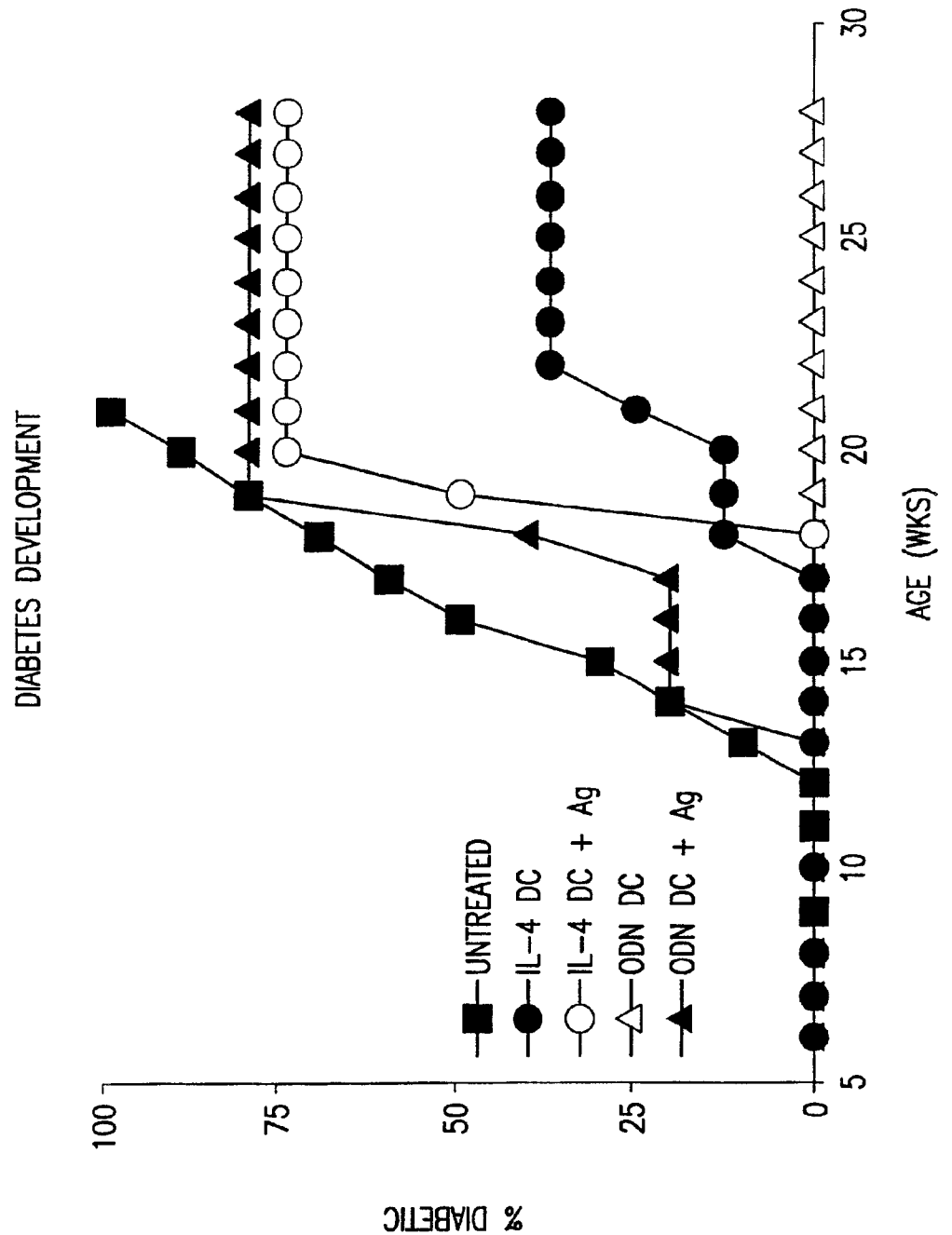
FIG. 16 is a graph showing that NF-κB ODN DC administration prevents the onset of Type 1 diabetes development in NOD mice.

FIG. 15 indicates that NOD bone marrow-derived IL-4 DC, but not NF-κB ODN DC, pulsed with islet antigen lysate, strongly induce T cell proliferation. In addition, NOD bone marrow-derived NF-κB ODN significantly inhibit CD80 and CD86 compared to NOD bone marrow-derived IL-4 DCs which expressed high levels of costimulatory molecules on their surface (see FIG. 15). Furthermore, NF-κB ODN DCs inhibited diabetes development in NOD mice dramatically. FIG. 16 shows 100% of NOD mice treated with NF-κB ODN DCs had normal levels of serum glucose at the age of 32 weeks whereas 100% of untreated mice developed diabetes before the age of 17 weeks. These data indicate that NF-κB DCs are useful for the treatment of diabetes.

We claim:

1. An isolated tolerogenic dendritic cell comprising an oligodeoxyribonucleotide having one or more NF-κB binding sites, wherein the oligodeoxyribonucleotide inhibits NF-κB transcriptional activity, and wherein the oligodeoxyribonucleotide has the sequence set forth in SEQ ID NO:1.

2. The isolated tolerogenic dendritic cell of claim 1 wherein the oligodeoxyribonucleotide sequence has two NF-κB binding sites.

3. A method of producing an isolated tolerogenic dendritic cell comprising (a) propagating an immature isolated dendritic cell from a mammalian donor, (b) incubating the immature isolated dendritic cell with an oligodeoxyribonucleotide having at least one NF-κB binding site under conditions wherein the immature isolated dendritic cell internalizes the oligodeoxyribonucleotide, wherein the oligodeoxyribonucleotide inhibits NF-κB transcriptional activity and (c) culturing the isolated dendritic cell of (b) to produce the isolated tolerogenic dendritic cell, and wherein the oligodeoxyribonucleotide has the sequence set forth in SEQ ID NO: 1.

4. The method of claim 3 further comprising incubating the isolated tolerogenic dendritic cell in the presence of one or more cytokine(s).

5. The method of claim 4 wherein the cytokine is GM-CSF.

6. The method of claim 4 further comprising incubating the isolated tolerogenic dendritic cell in the presence of TGF-β.

7. A kit for enhancing tolerogenicity in a mammalian host comprising tolerogenic dendritic cells which comprise an oligodeoxyribonucleotide having at least one NF-κB binding site, wherein the oligodeoxyribonucleotide inhibits NF-κB transcriptional activity, and wherein the oligodeoxyribonucleotide has a sequence set forth in SEQ ID NO:1.

* * * * *

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Synthesized nucleotide sequence

<400> SEQUENCE: 1
agggactttc cgctggggac tttcc                                          25

<210> SEQ ID NO 2
<211> LENGTH: 25
<212> TYPE: DNA
<213> ORGANISM: Artificial Sequence
<220> FEATURE:
<223> OTHER INFORMATION: Synthesized nucleotide sequence

<400> SEQUENCE: 2
ggaaagtccc cagcggaaag tccct                                          25

<210> SEQ ID NO 3
<211> LENGTH: 25
<212> TYPE: DNA
<213> ORGANISM: Artificial Sequence
<220> FEATURE:
<223> OTHER INFORMATION: Synthesized nucleotide sequence

<400> SEQUENCE: 3
accagtccct agctaccagt cccta                                          25

<210> SEQ ID NO 4
<211> LENGTH: 25
<212> TYPE: DNA
<213> ORGANISM: Artificial Sequence
<220> FEATURE:
<223> OTHER INFORMATION: Synthesized nucleotide sequence

<400> SEQUENCE: 4
tagggactgg tagctaggga ctggt                                          25

<210> SEQ ID NO 5
<211> LENGTH: 25
<212> TYPE: DNA
<213> ORGANISM: Artificial Sequence
<220> FEATURE:
<223> OTHER INFORMATION: Synthesized nucleotide sequence

<400> SEQUENCE: 5
aggtactgtc cgcgttagac gtgcc                                          25

<210> SEQ ID NO 6
<211> LENGTH: 25
<212> TYPE: DNA
<213> ORGANISM: Artificial Sequence
<220> FEATURE:
<223> OTHER INFORMATION: Synthesized nucleotide sequence

<400> SEQUENCE: 6
ggcacgtcta acgcggacag tacct                                          25

<210> SEQ ID NO 7
<211> LENGTH: 22

```
<212> TYPE: DNA
<213> ORGANISM: Artificial Sequence
<220> FEATURE:
<223> OTHER INFORMATION: Synthesized nucleotide sequence

<400> SEQUENCE: 7
agttgagggg actttcccag gc                                              22
```